United States Patent
Ahrens et al.

(10) Patent No.: US 9,988,347 B2
(45) Date of Patent: Jun. 5, 2018

(54) HERBICIDALLY ACTIVE ARYLCARBOXYLIC ACID AMIDES

(71) Applicant: BAYER CROPSCIENCE AKTIENGESELLSCHAFT, Monheim am Rhein (DE)

(72) Inventors: Hartmut Ahrens, Egelsbach (DE); Joerg Tiebes, Frankfurt (DE); Christian Waldraff, Bad Vilbel (DE); Hansjoerg Dietrich, Liederbach am Taunus (DE); Elmar Gatzweiler, Bad Nauheim (DE); Christopher Hugh Rosinger, Hofheim am Taunus (GB); Dirk Schmutzler, Hattersheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days. days.

(21) Appl. No.: 15/320,828

(22) PCT Filed: Jun. 26, 2015

(86) PCT No.: PCT/EP2015/064484
§ 371 (c)(1),
(2) Date: Dec. 21, 2016

(87) PCT Pub. No.: WO2016/001073
PCT Pub. Date: Jan. 7, 2016

(65) Prior Publication Data
US 2017/0158629 A1  Jun. 8, 2017

(30) Foreign Application Priority Data
Jun. 30, 2014 (EP) .................................... 14174873

(51) Int. Cl.
| | |
|---|---|
| *C07D 249/14* | (2006.01) |
| *C07D 257/06* | (2006.01) |
| *C07D 271/08* | (2006.01) |
| *C07D 271/113* | (2006.01) |
| *A01N 43/713* | (2006.01) |
| *A01N 43/653* | (2006.01) |
| *A01N 43/82* | (2006.01) |
| *C07C 317/44* | (2006.01) |
| *C07C 323/56* | (2006.01) |
| *C07D 271/04* | (2006.01) |
| *C07D 271/10* | (2006.01) |

(52) U.S. Cl.
CPC .......... *C07C 317/44* (2013.01); *A01N 43/653* (2013.01); *A01N 43/713* (2013.01); *A01N 43/82* (2013.01); *C07C 323/56* (2013.01); *C07D 249/14* (2013.01); *C07D 257/06* (2013.01); *C07D 271/04* (2013.01); *C07D 271/08* (2013.01); *C07D 271/10* (2013.01); *C07D 271/113* (2013.01)

(58) Field of Classification Search
CPC .. C07D 257/06; C07D 249/14; C07D 271/08; C07D 271/113; A01N 43/713; A01N 43/653; A01N 43/82
See application file for complete search history.

(56) References Cited

U.S. PATENT DOCUMENTS

| | | |
|---|---|---|
| 2011/0152084 A1 | 6/2011 | Koehn et al. |
| 2012/0058892 A1* | 3/2012 | Braun .................. A01N 43/653 504/103 |
| 2014/0080705 A1 | 3/2014 | Koehn et al. |

FOREIGN PATENT DOCUMENTS

| | | |
|---|---|---|
| WO | 2011/035874 A1 | 3/2011 |
| WO | 2012/126932 A1 | 3/2012 |
| WO | 2012028579 A1 | 3/2012 |

OTHER PUBLICATIONS

International Search Report of PCT/EP2015/064484 dated Aug. 17, 2015.

* cited by examiner

*Primary Examiner* — John Pak
(74) *Attorney, Agent, or Firm* — McBee Moore Woodward & Vanik IP, LLC

(57) ABSTRACT

Benzamides of the general formula (I) are described as herbicides.

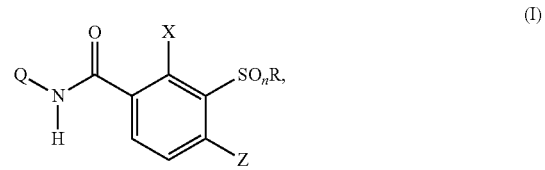

(I)

In this formula (I), X, Z and R are radicals such as alkyl and cycloalkyl. Q is a 5-membered heterocycle.

9 Claims, No Drawings

HERBICIDALLY ACTIVE ARYLCARBOXYLIC ACID AMIDES

CROSS REFERENCE TO RELATED APPLICATIONS

This application is a § 371 National State Application of PCT/EP2015/064484, filed Jun. 26, 2015, which claims priority to European Application No. 14174873.1 filed Jun. 30, 2014.

BACKGROUND OF THE INVENTION

Field of the Invention

The invention relates to the technical field of the herbicides, especially that of the herbicides for selective control of broad-leaved weeds and weed grasses in crops of useful plants.

Description of Related Art

WO 2012/028579 A1 discloses N-(tetrazol-5-yl)- and N-(triazol-5-yl)arylcarboxamides and use thereof as herbicides. WO 2012/126932 A1 describes N-(1,3,4-oxadiazol-2-yl)arylcarboxamides and use thereof as herbicides. The active ingredients described therein do not always exhibit sufficient activity against harmful plants and/or some do not have sufficient compatibility with some important crop plants such as cereal species, corn and rice.

SUMMARY

It is an object of the present invention to provide alternative herbicidally active ingredients. This object is achieved by the arylcarboxamides of the invention that are described hereinafter, which bear an alkyl or cycloalkyl radical in the 2 position, a sulfur radical in the 3 position and a cycloalkyl radical in the 4 position.

The present invention thus provides arylcarboxamides of the formula (I) or salts thereof

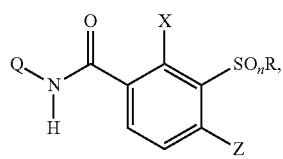

where the symbols and indices are each defined as follows:
Q is a Q1, Q2, Q3 or Q4 radical,

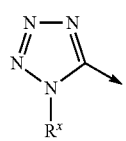

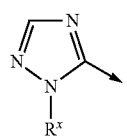

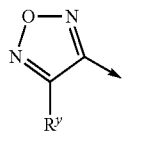

X is $(C_1-C_6)$-alkyl or $(C_3-C_6)$-cycloalkyl,
Z is $(C_3-C_6)$-cycloalkyl,
R is $(C_1-C_6)$-alkyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl,
$R^X$ is methyl, ethyl, n-propyl, prop-2-en-1-yl, methoxyethyl, ethoxyethyl or methoxyethoxyethyl,
$R^Y$ is methyl, ethyl, n-propyl, chlorine or amino,
$R^Z$ is methyl, ethyl, n-propyl or methoxymethyl,
n is 0, 1 or 2.

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

If a group is polysubstituted by radicals, this is to be understood as meaning that this group is substituted by one or more identical or different radicals selected from the radicals mentioned.

Depending on the nature of the substituents and the manner in which they are attached, the compounds of the general formula (I) may be present as stereoisomers. If, for example, one or more asymmetrically substituted carbon atoms are present, there may be enantiomers and diastereomers. Stereoisomers likewise occur when n represents 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically.

The compounds of the formula (I) are capable of forming salts. Salts may be formed by action of a base on compounds of the formula (I). Examples of suitable bases are organic amines such as trialkylamines, morpholine, piperidine and pyridine, and the hydroxides, carbonates and hydrogencarbonates of ammonium, alkali metals or alkaline earth metals, especially sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula $[NR^aR^bR^cR^d]^+$ in which $R^a$ to $R^d$ are each independently an organic radical, especially alkyl, aryl, aralkyl or alkylaryl. Also suitable are alkylsulfonium and alkylsulfoxonium salts, such as $(C_1-C_4)$-trialkylsulfonium and $(C_1-C_4)$-trialkylsulfoxonium salts.

DETAILED DESCRIPTION OF A PREFERRED EMBODIMENT

Preference is given to compounds of the general formula (I) in which
Q is a Q1, Q2, Q3 or Q4 radical,

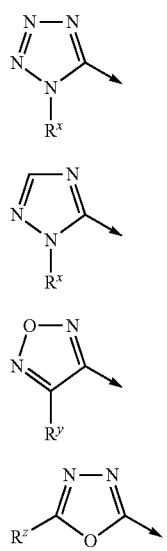

X is methyl, ethyl or cyclopropyl,
Z is cyclopropyl or cyclobutyl,
R is methyl, ethyl, cyclopropyl, cyclopropylmethyl or methoxyethyl,
$R^X$ is methyl, ethyl, n-propyl, prop-2-en-1-yl, methoxyethyl, ethoxyethyl or methoxyethoxyethyl,
$R^Y$ is methyl, ethyl, n-propyl, chlorine or amino,
$R^Z$ is methyl, ethyl, n-propyl or methoxymethyl,
n is 0, 1 or 2.

In all the formulae specified hereinafter, the substituents and symbols have the same meaning as described in formula (I), unless defined differently.

Compounds of the invention in which Q is Q1 or Q2, and the aminotetrazoles and aminotriazoles that underlie these amides, can be prepared, for example, by the methods specified in WO 2012/028579.

Compounds of the invention in which Q is Q3, and the aminofurazans that underlie these amides, can be prepared, for example, by the methods specified in WO 2011/035874.

Compounds of the invention in which Q is Q4 can be prepared, for example, by the methods specified in WO 2012/126932. The 2-amino-1,3,4-oxadiazoles that underlie these amides are commercially available or synthetically obtainable by standard methods that are well-described in the literature.

The benzoyl chlorides that underlie the compounds of the invention, or the corresponding benzoic acids, can be prepared, for example, by the method shown in scheme 1 (by way of example for the R radical=methyl). For this purpose, 1-bromo-3-fluorobenzene is subjected to a lithiation which is directed to the 2 position. The carbanion is then converted to the thioether. Thereafter, the benzoic acid is synthesized via an ortho-directing lithiation mediated by the fluorine atom with subsequent carboxylation (Matthew D. Morrison et al., Organic Letters, 2009, vol. 11, #p. 1051-1054; Qiuping Wang et al., Journal of Medicinal Chemistry, 2007, vol. 50, #2 p. 199-210). After the formation of the oxazoline group, the fluorine atom can be nucleophilically exchanged for alkyl or cycloalkyl radicals (A. I. Meyers et al., Tetrahedron Letters, 1978, 3, 223-226; A. I. Meyers et al., Tetrahedron, 1994, 50 (8), 2297-2360; T. W. Greene, P. G. M. Wuts, Protective Groups in Organic Synthesis, 2nd Edition, John Wiley & Sons, Inc. 1991, S. 265 ff.; Z. Hell et al., Tetrahedron Letters, 2002, 43, 3985-3987.). The subsequent oxazoline cleavage affords the substituted 4-bromo-3-methylthiobenzoic acid, which is subjected in the form of the methyl ester to a cross-coupling. With the incorporation of the substituent in the 4 position and the subsequent ester hydrolysis, the synthesis of the benzoic acid is complete.

Scheme 1

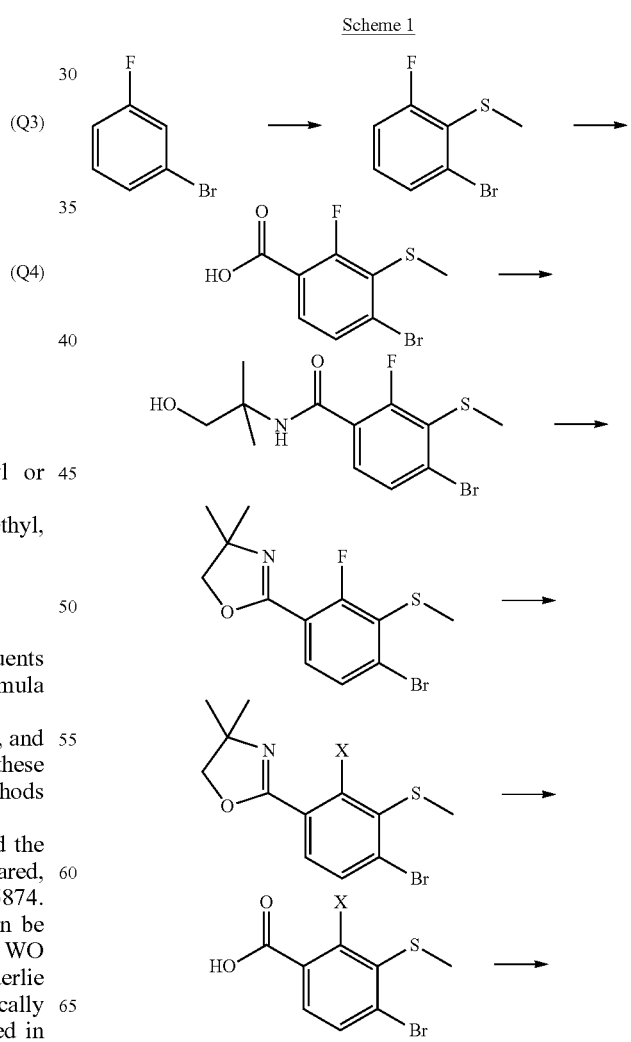

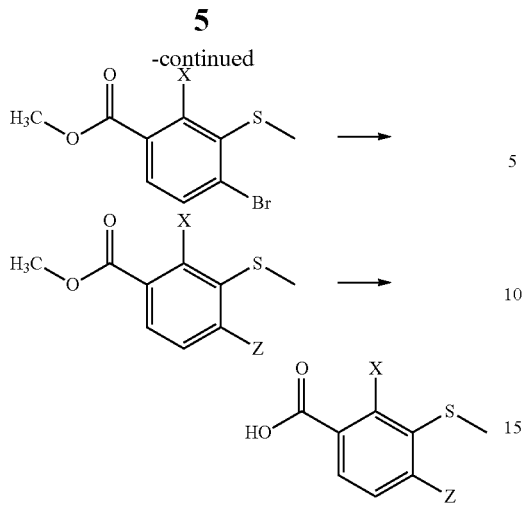

The thioether can be oxidized further to the corresponding sulfoxide or sulfone (scheme 2). Oxidation methods that lead selectively to the sulfoxide or sulfone are known from the literature. There are a number of possible oxidation systems, for example peracids such as meta-chloroperbenzoic acid, which is optionally generated in situ (for example peracetic acid in the acetic acid/hydrogen peroxide/sodium tungstate(VI) system) (Houben-Weyl, Methoden der Organischen Chemie [Methods of Organic Chemistry], Georg Thieme Verlag Stuttgart, Vol. E 11, expanded and supplementary volumes to the 4th edition 1985, p. 702 ff., p. 718 ff. and p. 1194 ff.).

The substitution pattern and the oxidizing agent are among the factors that decide the point in the synthesis cascade at which the oxidation of the thioether is appropriate. An oxidation may be appropriate, for example, at the stage of the free benzoic acid or at the stage of the amide of the formula (I) with n=0 (scheme 2).

Scheme 2

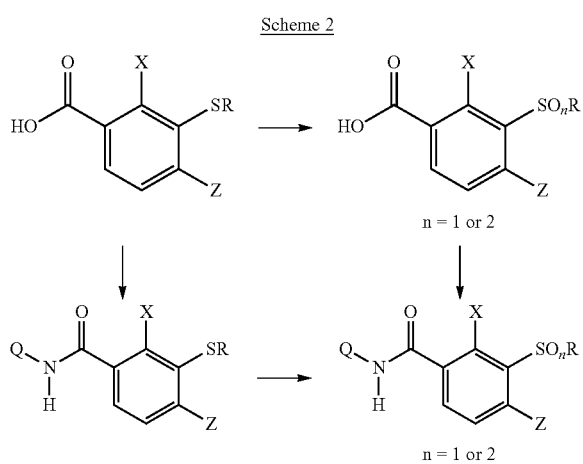

It may be appropriate to alter the sequence of the reaction steps. For instance, benzoic acids bearing a sulfoxide cannot be converted directly to their acid chlorides. One option here is first to prepare the amide of the formula (I) with n=0 at the thioether stage and then to oxidize the thioether to the sulfoxide.

The workup of the respective reaction mixtures is generally effected by known processes, for example by crystallization, aqueous-extractive workup, by chromatographic methods or by a combination of these methods.

The benzoic acids of the formula (II) and benzoyl chlorides of the formula (III) which are utilized as intermediates in the preparation of the inventive compounds of the formula (I) are novel and likewise form part of the subject matter of the present invention.

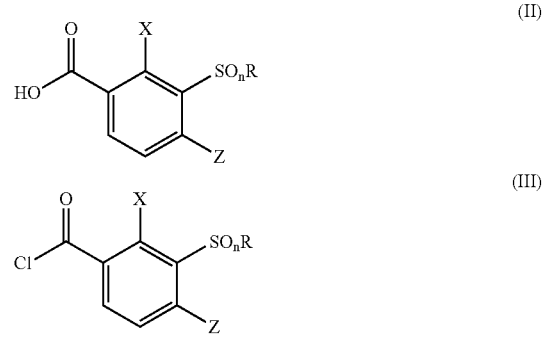

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor Ginther Jung), Wiley, 1999, on pages 1 to 34. For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich). Aside from the methods described here, compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Ginther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, the conduction of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The compounds of the invention have excellent herbicidal efficacy against a broad spectrum of economically important mono- and dicotyledonous annual harmful plants. The active ingredients also act efficiently on perennial weeds which produce shoots from rhizomes, root stocks and other perennial organs and which are difficult to control.

The present invention therefore also provides a method for controlling unwanted plants or for regulating the growth of plants, preferably in plant crops, in which one or more compound(s) according to the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though there is no intention to restrict the enumeration to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria* and *Sorghum*.

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola* and *Xanthium*.

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage at the time of application, or they die completely after a certain time, such that competition by the weeds, which is harmful to the crop plants, is thus eliminated very early and in a lasting manner.

Although the compounds of the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, will be damaged to a negligible extent only, if at all, depending on the structure of the particular compound of the invention and its application rate. For these reasons, the present compounds are very suitable for selective control of unwanted plant growth in plant crops such as agriculturally useful plants or ornamental plants.

In addition, the compounds of the invention, depending on their particular chemical structure and the application rate deployed, have outstanding growth-regulating properties in crop plants. They intervene in the plants' own metabolism with regulatory effect, and can thus be used for controlled influencing of plant constituents and to facilitate harvesting, for example by triggering desiccation and stunted growth. In addition, they are also suitable for general control and inhibition of unwanted vegetative growth without killing the plants. Inhibition of vegetative growth plays a major role for many mono- and dicotyledonous crops since, for example, this can reduce or completely prevent lodging.

By virtue of their herbicidal and plant growth regulatory properties, the active compounds can also be used to control harmful plants in crops of genetically modified plants which are known or are yet to be developed. In general, transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further special properties may be tolerance or resistance to abiotic stress factors, for example heat, cold, drought, salinity and ultraviolet radiation.

Preference is given to the use of the inventive compounds of the formula (I) or salts thereof in economically important transgenic crops of useful plants and ornamental plants, for example of cereals such as wheat, barley, rye, oats, millet, rice, cassava and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods (see, for example, EP 0221044, EP 0131624). For example, there have been descriptions in several cases of:

- genetic modifications of crop plants for the purpose of modifying the starch synthesized in the plants (for example WO 92/011376 A, WO 92/014827 A, WO 91/019806 A),
- transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soya with the trade name or the designation Optimum™ GAT™ (Glyphosate ALS Tolerant),
- transgenic crop plants, for example cotton, capable of producing *Bacillus thuringiensis* toxins (Bt toxins), which make the plants resistant to particular pests (EP-A-0142924, EP-A-0193259),
- transgenic crop plants having a modified fatty acid composition (WO 91/013972 A),
- genetically modified crop plants having novel constituents or secondary metabolites, for example novel phytoalexins, which cause an increase in disease resistance (EP 0309862 A, EP 0464461 A),
- genetically modified plants having reduced photorespiration, which have higher yields and higher stress tolerance (EP 0305398 A),
- transgenic crop plants which produce pharmaceutically or diagnostically important proteins ("molecular pharming"),
- transgenic crop plants which feature higher yields or better quality,
- transgenic crop plants which are distinguished by a combination, for example of the abovementioned novel properties ("gene stacking").

Numerous molecular biology techniques which can be used to produce novel transgenic plants with modified properties are known in principle; see, for example, I. Potrykus and G. Spangenberg (eds.), Gene Transfer to Plants, Springer Lab Manual (1995), Springer Verlag Berlin, Heidelberg or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene und Klone", VCH Weinheim, 2nd edition, 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences. The inventive compounds (I) can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients, or to any desired combinations of these active ingredients.

The compounds of the invention can be used with particular preference in transgenic crop plants which are resistant to a combination of glyphosates and glufosinates, glyphosates and sulfonylureas or imidazolinones. The compounds of the invention can be used with very particular preference in transgenic crop plants, for example corn or soybeans with the trade name or the designation Optimum™ GAT™ (glyphosate ALS tolerant).

When the active ingredients of the invention are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the formula (I) according to the invention as herbicides for controlling harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: Wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie", Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte" [Interface-active Ethylene Oxide Adducts], Wiss. Verlagsgesell., Stuttgart 1976, Winnacker-Küchler, "Chemische Technologie", Volume 7, C. Hanser Verlag Munich, 4th ed. 1986.

Wettable powders are preparations which can be dispersed uniformly in water and, in addition to the active ingredient, apart from a diluent or inert substance, also comprise surfactants of the ionic and/or nonionic type (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active ingredients are finely ground, for example in customary apparatus such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active ingredient with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan, fluidized-bed, extruder and spray granules, see e.g. processes in "Spray Drying Handbook" 3rd Ed. 1979, G. Goodwin Ltd., London, J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention.

In wettable powders, the active ingredient concentration is, for example, about 10% to 90% by weight, the remainder to 100% by weight consisting of customary formulation constituents. In emulsifiable concentrates, the active ingredient concentration may be about 1% to 90% and preferably 5% to 80% by weight. Dust-type formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active compound is present in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more of active substance, but it is preferably between 0.005 and 750 g/ha.

The examples below illustrate the invention.

A. CHEMICAL EXAMPLES

4-Cyclopropyl-2-methyl-3-(methylsulfinyl)-N-(1-methyl-1H-tetrazol-5-yl)benzamide (Example No. 1-2)

Step 1: Synthesis of 1-bromo-3-fluoro-2-(methylsulfanyl)benzene 1028 mL of a 2.5 M (2.57 mol) solution of n-butyllithium in n-hexane were dissolved in 1600 mL of dry THF. At 0° C., 400 mL (2.83 mol) of diisopropylamine were added. The reaction mixture was stirred at this temperature for 15 min. The mixture was then cooled down to −78° C. At this temperature, 287 mL (2.57 mol) of 1-bromo-3-fluorobenzene were added dropwise. The mixture was stirred at this temperature for 1 h. Thereafter, 254 mL (2.82 mol) of dimethyl disulfide were added. Subsequently, the reaction mixture was thawed to room temperature (RT). After the aqueous workup, the residue of the organic phase was subjected to a fractional distillation at 0.5 mbar. At 87° C., 504 g of the desired product were obtained.

Step 2: Synthesis of 4-bromo-2-fluoro-3-(methylsulfanyl)benzoic acid 452 mL of a 2.5 M (1.13 mol) solution of n-butyllithium in n-hexane were added dropwise at −78° C. to a solution of 176 mL (1.24 mol) of diisopropylamine in 550 mL of dry THF. The solution was stirred at this temperature for 5 min and then at 0° C. for 15 min. Thereafter, the solution was cooled back down to −78° C. Subsequently, a solution of 250 g (1.13 mol) of 1-bromo-3-fluoro-2-(methylsulfanyl)benzene in 150 mL of dry THF was added dropwise. The solution was stirred at −78° C. for 1.5 h. Thereafter, 298 g (6.78 mol) of carbon dioxide were added in the form of dry ice. The reaction mixture was thawed gradually to RT. For workup, the mixture was acidified to pH=1 with dilute hydrochloric acid. The product was then extracted six times with diethyl ether. The combined organic phases were washed with a saturated aqueous sodium chloride solution. Subsequently, the product was extracted three times with a saturated aqueous sodium hydrogencarbonate solution. The combined aqueous extracts were washed three times with diethyl ether at pH=9 and then acidified gradually to pH=1 with concentrated hydrochloric acid. The product was extracted three times with diethyl ether, and the combined organic phases were washed with a saturated aqueous sodium chloride solution. Finally, the combined organic phases were dried over magnesium sulfate, and the filtrate was freed of the solvent. For further purification, the product was recrystallized from water, and 275 g of the desired product were obtained.

Step 3: Synthesis of 4-bromo-2-fluoro-N-(1-hydroxy-2-methylpropan-2-yl)-3-(methylsulfanyl)benzamide To 340 g (1.28 mol) of 4-bromo-2-fluoro-3-(methylsulfanyl)benzoic acid in 1000 mL of dry dichloromethane were added 2 mL of N,N-dimethylformamide, and then the mixture was heated to a temperature of 35° C. 271 mL (3.20 mol) of oxalyl chloride were slowly added dropwise at this temperature. On conclusion of the evolution of gas, the reaction mixture was heated under reflux until the monitoring of the reaction no longer indicated any starting material. Subsequently, the mixture was freed of the solvent. 600 mL of toluene were added to the residue and the mixture was freed of the solvent once again. The acid chloride was taken up in 600 mL of anhydrous dichloromethane. At 5° C.-25° C., this solution was added dropwise to a mixture of 305 mL (3.20 mol) of 2-amino-2-methylpropan-1-ol and 100 mL of anhydrous dichloromethane. The reaction mixture was stirred at 0° C. for 1.5 h and then at room temperature for 16 h. For workup, the mixture was filtered and the filtrate was freed of the solvent. The residue obtained was 330 g of product, which was used without further purification in the next step.

Step 4: Synthesis of 2-[4-bromo-2-fluoro-3-(methylsulfanyl)phenyl]-4,4-dimethyl-4,5-dihydro-1,3-oxazole To 330 g (0.98 mol) of 4-bromo-2-fluoro-N-(1-hydroxy-2-methylpropan-2-yl)-3-(methylsulfanyl)benzamide were added, at RT, 384 mL (5.3 mol) of thionyl chloride. On conclusion of the evolution of gas, the reaction mixture was stirred at RT for another 1 h. For workup, the mixture was poured cautiously into water. Subsequently, the mixture was extracted with diethyl ether. The aqueous phase was cooled down to 00° C. and alkalized with 20 percent sodium hydroxide solution. The mixture was then immediately and rapidly extracted with dichloromethane. The organic phase was dried and the filtrate was freed of the solvent. The crude product was recrystallized from diisopropyl ether, and 165 g of the desired product were isolated.

Step 5: Synthesis of 2-[4-bromo-2-methyl-3-(methylsulfanyl)phenyl]-4,4-dimethyl-4,5-dihydro-1,3-oxazole To 45 g (141 mmol) of 2-[4-bromo-2-fluoro-3-(methylsulfanyl)phenyl]-4,4-dimethyl-4,5-dihydro-1,3-oxazole at RT in 440 mL of dry diethyl ether was slowly added dropwise, under protective gas, methylmagnesium iodide (freshly prepared from 12.37 g (507 mmol) of magnesium and 71.24 g (501 mmol) of iodomethane). It was ensured that the temperature did not rise above 30° C. Thereafter, the mixture was stirred at RT until the monitoring of the reaction no longer indicated any starting material. For workup, the mixture was poured gradually into a mixture of ice and dilute hydrochloric acid. Subsequently, sodium hydroxide solution was added until the pH was between 7 and 8. The aqueous phase was extracted twice with diethyl ether. The combined organic phases were dried and the filtrate was freed of the solvent. The residue was recrystallized from diisopropyl ether, and 38 g of the desired product were obtained.

Step 6: Synthesis of
4-bromo-2-methyl-3-(methylsulfanyl)benzoic acid

To 250 g (0.8 mol) of 2-[4-bromo-2-methyl-3-(methylsulfanyl)phenyl]-4,4-dimethyl-4,5-dihydro-1,3-oxazole were added 1300 mL of 6 M hydrochloric acid. The reaction mixture was heated under reflux for 24 h. For workup, the mixture was alkalized and washed twice with diethyl ether. The aqueous phase was acidified with hydrochloric acid. The product crystallized out and the mixture was filtered. 167 g of the desired product were obtained as residue.

Step 7: Synthesis of methyl
4-bromo-2-methyl-3-(methylsulfanyl)benzoate

To 10.1 g (38.7 mmol) of 4-bromo-2-methyl-3-(methylsulfanyl)benzoic acid in 100 mL of methanol were added 5 mL of concentrated sulfuric acid. The mixture was then heated under reflux for 8 h. The mixture was cooled to RT and freed of the solvent. The residue was taken up in water and cooled down in an ice bath. The mixture was filtered and the residue was washed with saturated aqueous sodium hydrogencarbonate solution. The residue was dried, and 9.82 g of the desired product were obtained.

Step 8: Synthesis of
4-cyclopropyl-2-methyl-3-(methylsulfanyl)benzoic
acid (Example No. 9-1)

To 1.94 g (80.0 mmol) of magnesium turnings under protective gas were added 5 mL of dry tetrahydrofuran. Subsequently, a small amount of the total of 9.67 g (80.0 mmol) of cyclopropyl bromide and a catalytic amount of iodine were added in order to initiate the Grignard reaction. After the Grignard reaction had started, the rest of the cyclopropyl bromide, which had been diluted beforehand with 145 mL of dry tetrahydrofuran, was slowly added dropwise. To complete the reaction, the mixture was then heated under reflux for 15 min. The contents were cooled to RT, then 800 mg (18.9 mmol) of lithium chloride were added. Once the lithium chloride had dissolved, the mixture was cooled down to −20° C. Subsequently, 114 mL (0.7 M; 79.8 mmol) of a solution of zinc chloride in dry tetrahydrofuran were slowly added dropwise. The mixture was stirred at this temperature for another 15 min. Subsequently, the contents were thawed to RT and, for removal of oxygen, there was repeated application of reduced pressure and venting with argon in the reaction flask. Added to this mixture was a solution of 10.0 g (36.3 mmol) of methyl 4-bromo-2-methyl-3-(methylsulfanyl)benzoate and 2.35 g (2.04 mmol) of tetrakis(triphenylphosphine)palladium(0) in 200 mL of dry tetrahydrofuran (made up by first dissolving the substituted benzoic ester, repeatedly applying reduced pressure and venting with argon in the vessel to remove oxygen, then adding the palladium catalyst and finally once again repeatedly applying reduced pressure and venting with argon to remove oxygen). The reaction mixture was heated under reflux for 3 h and then cooled down to RT. To complete the reaction, half the abovementioned amount of Grignard reagent was prepared once again and correspondingly reacted with the zinc chloride solution. After the oxygen removal as described above, this amount of coupling reagent was added to the cross-coupling mixture. In addition, half the abovementioned amount of palladium catalyst was also added. The reaction mixture was heated again under reflux until, after 2 h, no starting material was detectable any longer. For workup, the contents were cooled to RT and 500 mL of a saturated aqueous ammonium chloride solution were added. The mixture was extracted twice with diethyl ether. The combined organic phases were dried, filtered and finally freed of the solvent with sufficient caution that no product went over as well. The residue was dissolved in 100 mL of methanol, and 10 mL of 20 percent sodium hydroxide solution were added. The mixture was stirred at RT for 16 h and then at 60° C. for 3 h. Thereafter, the reaction mixture was heated under reflux until the monitoring of the reaction no longer indicated any starting material. The mixture was concentrated and the residue was taken up in water. The mixture was washed with dichloromethane and the aqueous phase was filtered through Celite. The filtrate was acidified with 6 M hydrochloric acid and extracted three times with dichloromethane. The combined organic phases were dried, and the filtrate was concentrated to about half the volume. The residue was extracted three times with percent sodium hydroxide solution. The combined aqueous phases were acidified with 6 M hydrochloric acid and stirred in an ice bath, and the product precipitated out. The mixture was filtered and dried. 7.31 g of the desired product were obtained.

Step 9: Synthesis of 4-cyclopropyl-2-methyl-3-
(methylsulfanyl)-N-(1-methyl-1H-tetrazol-5-yl)benzamide (Example No. 1-1)

To 330 mg (1.48 mmol) of 4-cyclopropyl-2-methyl-3-(methylsulfanyl)benzoic acid and 191 mg (98% purity; 1.89 mmol) of 5-amino-1-methyl-1H-tetrazole in 10 mL of pyridine were added 264 mg (2.08 mmol) of oxalyl chloride. The mixture was stirred at RT for 15 min and then at 50° C. for 2 h. To complete the conversion, the mixture was cooled down to RT and another quarter of the above-specified amount of oxalyl chloride was added. The mixture was stirred at 50° C. for another 2 h. For workup, the mixture was freed of the solvent. The residue was taken up in dichloromethane and a saturated aqueous sodium hydrogencarbonate solution, and stirred. After phase separation, the organic phase was freed of the solvent. The residue was taken up in toluene and the mixture was concentrated once again. The residue was purified chromatographically, and 320 mg of the desired product were isolated.

Step 10: Synthesis of 4-cyclopropyl-2-methyl-3-
(methylsulfinyl)-N-(1-methyl-1H-tetrazol-5-yl)benzamide (Example No. 1-2)

To 107 mg (0.35 mmol) of 4-cyclopropyl-2-methyl-3-(methylsulfanyl)-N-(1-methyl-1H-tetrazol-5-yl)benzamide at RT in 10 mL of glacial acetic acid were added 34.3 mg (35 percent; 0.35 mmol) of an aqueous hydrogen peroxide solution. The reaction mixture was stirred at RT until the monitoring of the reaction no longer indicated any starting material. For workup, solid sodium metabisulfite was added until no peroxides were detectable any longer. The mixture was freed of the solvent, and the residue was taken up in a little water. After addition of 1 M hydrochloric acid, the mixture was stirred for 10 min and then filtered. The residue was dried and 80.4 mg of the desired product were obtained.

The compounds listed in tables below are very particularly preferred.

The abbreviations used mean:
Me=methyl Et=ethyl Pr=propyl c-Pr=cyclopropyl

TABLE 1

Inventive compounds of the general formula (I) in which Q is Q1 and $R^x$ is a methyl group

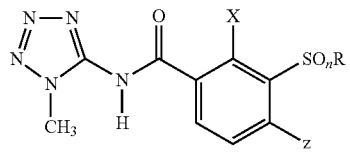

| No. | X | n | R | Z |
|---|---|---|---|---|
| 1-1 | Me | 0 | Me | c-Pr |
| 1-2 | Me | 1 | Me | c-Pr |
| 1-3 | Me | 2 | Me | c-Pr |
| 1-4 | Me | 0 | Et | c-Pr |
| 1-5 | Me | 1 | Et | c-Pr |
| 1-6 | Me | 2 | Et | c-Pr |
| 1-7 | Me | 0 | c-Pr | c-Pr |
| 1-8 | Me | 1 | c-Pr | c-Pr |
| 1-9 | Me | 2 | c-Pr | c-Pr |
| 1-10 | Me | 0 | $CH_2$c-Pr | c-Pr |
| 1-11 | Me | 1 | $CH_2$c-Pr | c-Pr |
| 1-12 | Me | 2 | $CH_2$c-Pr | c-Pr |
| 1-13 | Me | 0 | $CH_2CH_2$OMe | c-Pr |
| 1-14 | Me | 1 | $CH_2CH_2$OMe | c-Pr |
| 1-15 | Me | 2 | $CH_2CH_2$OMe | c-Pr |
| 1-16 | Me | 0 | Me | c-Bu |
| 1-17 | Me | 1 | Me | c-Bu |
| 1-18 | Me | 2 | Me | c-Bu |
| 1-19 | Me | 0 | Et | c-Bu |
| 1-20 | Me | 1 | Et | c-Bu |
| 1-21 | Me | 2 | Et | c-Bu |
| 1-22 | Me | 0 | c-Pr | c-Bu |
| 1-23 | Me | 1 | c-Pr | c-Bu |
| 1-24 | Me | 2 | c-Pr | c-Bu |
| 1-25 | Me | 0 | $CH_2$c-Pr | c-Bu |
| 1-26 | Me | 1 | $CH_2$c-Pr | c-Bu |
| 1-27 | Me | 2 | $CH_2$c-Pr | c-Bu |
| 1-28 | Me | 0 | $CH_2CH_2$OMe | c-Bu |
| 1-29 | Me | 1 | $CH_2CH_2$OMe | c-Bu |
| 1-30 | Me | 2 | $CH_2CH_2$OMe | c-Bu |
| 1-31 | Et | 0 | Me | c-Pr |
| 1-32 | Et | 1 | Me | c-Pr |
| 1-33 | Et | 2 | Me | c-Pr |
| 1-34 | Et | 0 | Et | c-Pr |
| 1-35 | Et | 1 | Et | c-Pr |
| 1-36 | Et | 2 | Et | c-Pr |
| 1-37 | Et | 0 | c-Pr | c-Pr |
| 1-38 | Et | 1 | c-Pr | c-Pr |
| 1-39 | Et | 2 | c-Pr | c-Pr |
| 1-40 | Et | 0 | $CH_2$c-Pr | c-Pr |
| 1-41 | Et | 1 | $CH_2$c-Pr | c-Pr |
| 1-42 | Et | 2 | $CH_2$c-Pr | c-Pr |
| 1-43 | Et | 0 | $CH_2CH_2$OMe | c-Pr |
| 1-44 | Et | 1 | $CH_2CH_2$OMe | c-Pr |
| 1-45 | Et | 2 | $CH_2CH_2$OMe | c-Pr |
| 1-46 | Et | 0 | Me | c-Bu |
| 1-47 | Et | 1 | Me | c-Bu |
| 1-48 | Et | 2 | Me | c-Bu |
| 1-49 | Et | 0 | Et | c-Bu |
| 1-50 | Et | 1 | Et | c-Bu |
| 1-51 | Et | 2 | Et | c-Bu |
| 1-52 | Et | 0 | c-Pr | c-Bu |
| 1-53 | Et | 1 | c-Pr | c-Bu |
| 1-54 | Et | 2 | c-Pr | c-Bu |
| 1-55 | Et | 0 | $CH_2$c-Pr | c-Bu |
| 1-56 | Et | 1 | $CH_2$c-Pr | c-Bu |
| 1-57 | Et | 2 | $CH_2$c-Pr | c-Bu |
| 1-58 | Et | 0 | $CH_2CH_2$OMe | c-Bu |
| 1-59 | Et | 1 | $CH_2CH_2$OMe | c-Bu |
| 1-60 | Et | 2 | $CH_2CH_2$OMe | c-Bu |
| 1-61 | c-Pr | 0 | Me | c-Pr |
| 1-62 | c-Pr | 1 | Me | c-Pr |
| 1-63 | c-Pr | 2 | Me | c-Pr |
| 1-64 | c-Pr | 0 | Et | c-Pr |
| 1-65 | c-Pr | 1 | Et | c-Pr |
| 1-66 | c-Pr | 2 | Et | c-Pr |
| 1-67 | c-Pr | 0 | c-Pr | c-Pr |
| 1-68 | c-Pr | 1 | c-Pr | c-Pr |
| 1-69 | c-Pr | 2 | c-Pr | c-Pr |
| 1-70 | c-Pr | 0 | $CH_2$c-Pr | c-Pr |
| 1-71 | c-Pr | 1 | $CH_2$c-Pr | c-Pr |
| 1-72 | c-Pr | 2 | $CH_2$c-Pr | c-Pr |
| 1-73 | c-Pr | 0 | $CH_2CH_2$OMe | c-Pr |
| 1-74 | c-Pr | 1 | $CH_2CH_2$OMe | c-Pr |
| 1-75 | c-Pr | 2 | $CH_2CH_2$OMe | c-Pr |
| 1-76 | c-Pr | 0 | Me | c-Bu |
| 1-77 | c-Pr | 1 | Me | c-Bu |
| 1-78 | c-Pr | 2 | Me | c-Bu |
| 1-79 | c-Pr | 0 | Et | c-Bu |
| 1-80 | c-Pr | 1 | Et | c-Bu |
| 1-81 | c-Pr | 2 | Et | c-Bu |
| 1-82 | c-Pr | 0 | c-Pr | c-Bu |
| 1-83 | c-Pr | 1 | c-Pr | c-Bu |
| 1-84 | c-Pr | 2 | c-Pr | c-Bu |
| 1-85 | c-Pr | 0 | $CH_2$c-Pr | c-Bu |
| 1-86 | c-Pr | 1 | $CH_2$c-Pr | c-Bu |
| 1-87 | c-Pr | 2 | $CH_2$c-Pr | c-Bu |
| 1-88 | c-Pr | 0 | $CH_2CH_2$OMe | c-Bu |
| 1-89 | c-Pr | 1 | $CH_2CH_2$OMe | c-Bu |
| 1-90 | c-Pr | 2 | $CH_2CH_2$OMe | c-Bu |

TABLE 2

Inventive compounds of the general formula (I) in which Q is Q1 and $R^x$ is a ethyl group

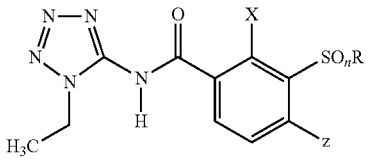

| No. | X | n | R | Z |
|---|---|---|---|---|
| 2-1 | Me | 0 | Me | c-Pr |
| 2-2 | Me | 1 | Me | c-Pr |
| 2-3 | Me | 2 | Me | c-Pr |
| 2-4 | Me | 0 | Et | c-Pr |
| 2-5 | Me | 1 | Et | c-Pr |
| 2-6 | Me | 2 | Et | c-Pr |
| 2-7 | Me | 0 | c-Pr | c-Pr |
| 2-8 | Me | 1 | c-Pr | c-Pr |
| 2-9 | Me | 2 | c-Pr | c-Pr |
| 2-10 | Me | 0 | $CH_2$c-Pr | c-Pr |
| 2-11 | Me | 1 | $CH_2$c-Pr | c-Pr |
| 2-12 | Me | 2 | $CH_2$c-Pr | c-Pr |
| 2-13 | Me | 0 | $CH_2CH_2$OMe | c-Pr |

TABLE 2-continued

Inventive compounds of the general formula (I) in which Q is Q1 and $R^x$ is a ethyl group

| No. | X | n | R | Z |
|---|---|---|---|---|
| 2-14 | Me | 1 | CH$_2$CH$_2$OMe | c-Pr |
| 2-15 | Me | 2 | CH$_2$CH$_2$OMe | c-Pr |
| 2-16 | Me | 0 | Me | c-Bu |
| 2-17 | Me | 1 | Me | c-Bu |
| 2-18 | Me | 2 | Me | c-Bu |
| 2-19 | Me | 0 | Et | c-Bu |
| 2-20 | Me | 1 | Et | c-Bu |
| 2-21 | Me | 2 | Et | c-Bu |
| 2-22 | Me | 0 | c-Pr | c-Bu |
| 2-23 | Me | 1 | c-Pr | c-Bu |
| 2-24 | Me | 2 | c-Pr | c-Bu |
| 2-25 | Me | 0 | CH$_2$c-Pr | c-Bu |
| 2-26 | Me | 1 | CH$_2$c-Pr | c-Bu |
| 2-27 | Me | 2 | CH$_2$c-Pr | c-Bu |
| 2-28 | Me | 0 | CH$_2$CH$_2$OMe | c-Bu |
| 2-29 | Me | 1 | CH$_2$CH$_2$OMe | c-Bu |
| 2-30 | Me | 2 | CH$_2$CH$_2$OMe | c-Bu |
| 2-31 | Et | 0 | Me | c-Pr |
| 2-32 | Et | 1 | Me | c-Pr |
| 2-33 | Et | 2 | Me | c-Pr |
| 2-34 | Et | 0 | Et | c-Pr |
| 2-35 | Et | 1 | Et | c-Pr |
| 2-36 | Et | 2 | Et | c-Pr |
| 2-37 | Et | 0 | c-Pr | c-Pr |
| 2-38 | Et | 1 | c-Pr | c-Pr |
| 2-39 | Et | 2 | c-Pr | c-Pr |
| 2-40 | Et | 0 | CH$_2$c-Pr | c-Pr |
| 2-41 | Et | 1 | CH$_2$c-Pr | c-Pr |
| 2-42 | Et | 2 | CH$_2$c-Pr | c-Pr |
| 2-43 | Et | 0 | CH$_2$CH$_2$OMe | c-Pr |
| 2-44 | Et | 1 | CH$_2$CH$_2$OMe | c-Pr |
| 2-45 | Et | 2 | CH$_2$CH$_2$OMe | c-Pr |
| 2-46 | Et | 0 | Me | c-Bu |
| 2-47 | Et | 1 | Me | c-Bu |
| 2-48 | Et | 2 | Me | c-Bu |
| 2-49 | Et | 0 | Et | c-Bu |
| 2-50 | Et | 1 | Et | c-Bu |
| 2-51 | Et | 2 | Et | c-Bu |
| 2-52 | Et | 0 | c-Pr | c-Bu |
| 2-53 | Et | 1 | c-Pr | c-Bu |
| 2-54 | Et | 2 | c-Pr | c-Bu |
| 2-55 | Et | 0 | CH$_2$c-Pr | c-Bu |
| 2-56 | Et | 1 | CH$_2$c-Pr | c-Bu |
| 2-57 | Et | 2 | CH$_2$c-Pr | c-Bu |
| 2-58 | Et | 0 | CH$_2$CH$_2$OMe | c-Bu |
| 2-59 | Et | 1 | CH$_2$CH$_2$OMe | c-Bu |
| 2-60 | Et | 2 | CH$_2$CH$_2$OMe | c-Bu |
| 2-61 | c-Pr | 0 | Me | c-Pr |
| 2-62 | c-Pr | 1 | Me | c-Pr |
| 2-63 | c-Pr | 2 | Me | c-Pr |
| 2-64 | c-Pr | 0 | Et | c-Pr |
| 2-65 | c-Pr | 1 | Et | c-Pr |
| 2-66 | c-Pr | 2 | Et | c-Pr |
| 2-67 | c-Pr | 0 | c-Pr | c-Pr |
| 2-68 | c-Pr | 1 | c-Pr | c-Pr |
| 2-69 | c-Pr | 2 | c-Pr | c-Pr |
| 2-70 | c-Pr | 0 | CH$_2$c-Pr | c-Pr |
| 2-71 | c-Pr | 1 | CH$_2$c-Pr | c-Pr |
| 2-72 | c-Pr | 2 | CH$_2$c-Pr | c-Pr |
| 2-73 | c-Pr | 0 | CH$_2$CH$_2$OMe | c-Pr |
| 2-74 | c-Pr | 1 | CH$_2$CH$_2$OMe | c-Pr |
| 2-75 | c-Pr | 2 | CH$_2$CH$_2$OMe | c-Pr |
| 2-76 | c-Pr | 0 | Me | c-Bu |
| 2-77 | c-Pr | 1 | Me | c-Bu |
| 2-78 | c-Pr | 2 | Me | c-Bu |
| 2-79 | c-Pr | 0 | Et | c-Bu |
| 2-80 | c-Pr | 1 | Et | c-Bu |
| 2-81 | c-Pr | 2 | Et | c-Bu |
| 2-82 | c-Pr | 0 | c-Pr | c-Bu |
| 2-83 | c-Pr | 1 | c-Pr | c-Bu |
| 2-84 | c-Pr | 2 | c-Pr | c-Bu |
| 2-85 | c-Pr | 0 | CH$_2$c-Pr | c-Bu |
| 2-86 | c-Pr | 1 | CH$_2$c-Pr | c-Bu |
| 2-87 | c-Pr | 2 | CH$_2$c-Pr | c-Bu |
| 2-88 | c-Pr | 0 | CH$_2$CH$_2$OMe | c-Bu |
| 2-89 | c-Pr | 1 | CH$_2$CH$_2$OMe | c-Bu |

TABLE 3

Inventive compounds of the general formula (I) in which Q is Q1 and $R^x$ is a n-propyl group

| No. | X | n | R | Z |
|---|---|---|---|---|
| 3-1 | Me | 0 | Me | c-Pr |
| 3-2 | Me | 1 | Me | c-Pr |
| 3-3 | Me | 2 | Me | c-Pr |
| 3-4 | Me | 0 | Et | c-Pr |
| 3-5 | Me | 1 | Et | c-Pr |
| 3-6 | Me | 2 | Et | c-Pr |
| 3-7 | Me | 0 | c-Pr | c-Pr |
| 3-8 | Me | 1 | c-Pr | c-Pr |
| 3-9 | Me | 2 | c-Pr | c-Pr |
| 3-10 | Me | 0 | CH$_2$c-Pr | c-Pr |
| 3-11 | Me | 1 | CH$_2$c-Pr | c-Pr |
| 3-12 | Me | 2 | CH$_2$c-Pr | c-Pr |
| 3-13 | Me | 0 | CH$_2$CH$_2$OMe | c-Pr |
| 3-14 | Me | 1 | CH$_2$CH$_2$OMe | c-Pr |
| 3-15 | Me | 2 | CH$_2$CH$_2$OMe | c-Pr |
| 3-16 | Me | 0 | Me | c-Bu |
| 3-17 | Me | 1 | Me | c-Bu |
| 3-18 | Me | 2 | Me | c-Bu |
| 3-19 | Me | 0 | Et | c-Bu |
| 3-20 | Me | 1 | Et | c-Bu |
| 3-21 | Me | 2 | Et | c-Bu |
| 3-22 | Me | 0 | c-Pr | c-Bu |
| 3-23 | Me | 1 | c-Pr | c-Bu |
| 3-24 | Me | 2 | c-Pr | c-Bu |
| 3-25 | Me | 0 | CH$_2$c-Pr | c-Bu |
| 3-26 | Me | 1 | CH$_2$c-Pr | c-Bu |
| 3-27 | Me | 2 | CH$_2$c-Pr | c-Bu |
| 3-28 | Me | 0 | CH$_2$CH$_2$OMe | c-Bu |
| 3-29 | Me | 1 | CH$_2$CH$_2$OMe | c-Bu |
| 3-30 | Me | 2 | CH$_2$CH$_2$OMe | c-Bu |
| 3-31 | Et | 0 | Me | c-Pr |
| 3-32 | Et | 1 | Me | c-Pr |
| 3-33 | Et | 2 | Me | c-Pr |
| 3-34 | Et | 0 | Et | c-Pr |
| 3-35 | Et | 1 | Et | c-Pr |
| 3-36 | Et | 2 | Et | c-Pr |
| 3-37 | Et | 0 | c-Pr | c-Pr |
| 3-38 | Et | 1 | c-Pr | c-Pr |

TABLE 3-continued

Inventive compounds of the general formula (I) in which Q is Q1 and R^x is a n-propyl group

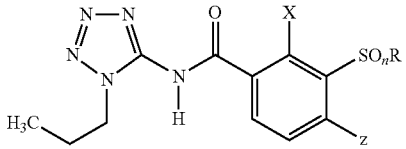

| No. | X | n | R | Z |
|---|---|---|---|---|
| 3-39 | Et | 2 | c-Pr | c-Pr |
| 3-40 | Et | 0 | CH$_2$c-Pr | c-Pr |
| 3-41 | Et | 1 | CH$_2$c-Pr | c-Pr |
| 3-42 | Et | 2 | CH$_2$c-Pr | c-Pr |
| 3-43 | Et | 0 | CH$_2$CH$_2$OMe | c-Pr |
| 3-44 | Et | 1 | CH$_2$CH$_2$OMe | c-Pr |
| 3-45 | Et | 2 | CH$_2$CH$_2$OMe | c-Pr |
| 3-46 | Et | 0 | Me | c-Bu |
| 3-47 | Et | 1 | Me | c-Bu |
| 3-48 | Et | 2 | Me | c-Bu |
| 3-49 | Et | 0 | Et | c-Bu |
| 3-50 | Et | 1 | Et | c-Bu |
| 3-51 | Et | 2 | Et | c-Bu |
| 3-52 | Et | 0 | c-Pr | c-Bu |
| 3-53 | Et | 1 | c-Pr | c-Bu |
| 3-54 | Et | 2 | c-Pr | c-Bu |
| 3-55 | Et | 0 | CH$_2$c-Pr | c-Bu |
| 3-56 | Et | 1 | CH$_2$c-Pr | c-Bu |
| 3-57 | Et | 2 | CH$_2$c-Pr | c-Bu |
| 3-58 | Et | 0 | CH$_2$CH$_2$OMe | c-Bu |
| 3-59 | Et | 1 | CH$_2$CH$_2$OMe | c-Bu |
| 3-60 | Et | 2 | CH$_2$CH$_2$OMe | c-Bu |
| 3-61 | c-Pr | 0 | Me | c-Pr |
| 3-62 | c-Pr | 1 | Me | c-Pr |
| 3-63 | c-Pr | 2 | Me | c-Pr |
| 3-64 | c-Pr | 0 | Et | c-Pr |
| 3-65 | c-Pr | 1 | Et | c-Pr |
| 3-66 | c-Pr | 2 | Et | c-Pr |
| 3-67 | c-Pr | 0 | c-Pr | c-Pr |
| 3-68 | c-Pr | 1 | c-Pr | c-Pr |
| 3-69 | c-Pr | 2 | c-Pr | c-Pr |
| 3-70 | c-Pr | 0 | CH$_2$c-Pr | c-Pr |
| 3-71 | c-Pr | 1 | CH$_2$c-Pr | c-Pr |
| 3-72 | c-Pr | 2 | CH$_2$c-Pr | c-Pr |
| 3-73 | c-Pr | 0 | CH$_2$CH$_2$OMe | c-Pr |
| 3-74 | c-Pr | 1 | CH$_2$CH$_2$OMe | c-Pr |
| 3-75 | c-Pr | 2 | CH$_2$CH$_2$OMe | c-Pr |
| 3-76 | c-Pr | 0 | Me | c-Bu |
| 3-77 | c-Pr | 1 | Me | c-Bu |
| 3-78 | c-Pr | 2 | Me | c-Bu |
| 3-79 | c-Pr | 0 | Et | c-Bu |
| 3-80 | c-Pr | 1 | Et | c-Bu |
| 3-81 | c-Pr | 2 | Et | c-Bu |
| 3-82 | c-Pr | 0 | c-Pr | c-Bu |
|  | c-Pr | 1 | c-Pr | c-Bu |
| 3-83 | c-Pr | 2 | c-Pr | c-Bu |
| 3-84 | c-Pr | 0 | CH$_2$c-Pr | c-Bu |
| 3-85 | c-Pr | 1 | CH$_2$c-Pr | c-Bu |
| 3-86 | c-Pr | 2 | CH$_2$c-Pr | c-Bu |
| 3-87 | c-Pr | 0 | CH$_2$CH$_2$OMe | c-Bu |
| 3-88 | c-Pr | 1 | CH$_2$CH$_2$OMe | c-Bu |
| 3-89 | c-Pr | 2 | CH$_2$CH$_2$OMe | c-Bu |

TABLE 4

Inventive compounds of the general formula (I) in which Q is Q2 and R^x is a methyl group

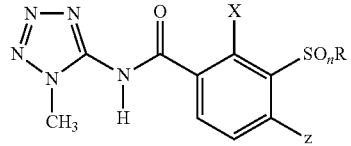

| No. | X | n | R | Z |
|---|---|---|---|---|
| 4-1 | Me | 0 | Me | c-Pr |
| 4-2 | Me | 1 | Me | c-Pr |
| 4-3 | Me | 2 | Me | c-Pr |
| 4-4 | Me | 0 | Et | c-Pr |
| 4-5 | Me | 1 | Et | c-Pr |
| 4-6 | Me | 2 | Et | c-Pr |
| 4-7 | Me | 0 | c-Pr | c-Pr |
| 4-8 | Me | 1 | c-Pr | c-Pr |
| 4-9 | Me | 2 | c-Pr | c-Pr |
| 4-10 | Me | 0 | CH$_2$c-Pr | c-Pr |
| 4-11 | Me | 1 | CH$_2$c-Pr | c-Pr |
| 4-12 | Me | 2 | CH$_2$c-Pr | c-Pr |
| 4-13 | Me | 0 | CH$_2$CH$_2$OMe | c-Pr |
| 4-14 | Me | 1 | CH$_2$CH$_2$OMe | c-Pr |
| 4-15 | Me | 2 | CH$_2$CH$_2$OMe | c-Pr |
| 4-16 | Me | 0 | Me | c-Bu |
| 4-17 | Me | 1 | Me | c-Bu |
| 4-18 | Me | 2 | Me | c-Bu |
| 4-19 | Me | 0 | Et | c-Bu |
| 4-20 | Me | 1 | Et | c-Bu |
| 4-21 | Me | 2 | Et | c-Bu |
| 4-22 | Me | 0 | c-Pr | c-Bu |
| 4-23 | Me | 1 | c-Pr | c-Bu |
| 4-24 | Me | 2 | c-Pr | c-Bu |
| 4-25 | Me | 0 | CH$_2$c-Pr | c-Bu |
| 4-26 | Me | 1 | CH$_2$c-Pr | c-Bu |
| 4-27 | Me | 2 | CH$_2$c-Pr | c-Bu |
| 4-28 | Me | 0 | CH$_2$CH$_2$OMe | c-Bu |
| 4-29 | Me | 1 | CH$_2$CH$_2$OMe | c-Bu |
| 4-30 | Me | 2 | CH$_2$CH$_2$OMe | c-Bu |
| 4-31 | Et | 0 | Me | c-Pr |
| 4-32 | Et | 1 | Me | c-Pr |
| 4-33 | Et | 2 | Me | c-Pr |
| 4-34 | Et | 0 | Et | c-Pr |
| 4-35 | Et | 1 | Et | c-Pr |
| 4-36 | Et | 2 | Et | c-Pr |
| 4-37 | Et | 0 | c-Pr | c-Pr |
| 4-38 | Et | 1 | c-Pr | c-Pr |
| 4-39 | Et | 2 | c-Pr | c-Pr |
| 4-40 | Et | 0 | CH$_2$c-Pr | c-Pr |
| 4-41 | Et | 1 | CH$_2$c-Pr | c-Pr |
| 4-42 | Et | 2 | CH$_2$c-Pr | c-Pr |
| 4-43 | Et | 0 | CH$_2$CH$_2$OMe | c-Pr |
| 4-44 | Et | 1 | CH$_2$CH$_2$OMe | c-Pr |
| 4-45 | Et | 2 | CH$_2$CH$_2$OMe | c-Pr |
| 4-46 | Et | 0 | Me | c-Bu |
| 4-47 | Et | 1 | Me | c-Bu |
| 4-48 | Et | 2 | Me | c-Bu |
| 4-49 | Et | 0 | Et | c-Bu |
| 4-50 | Et | 1 | Et | c-Bu |
| 4-51 | Et | 2 | Et | c-Bu |
| 4-52 | Et | 0 | c-Pr | c-Bu |
| 4-53 | Et | 1 | c-Pr | c-Bu |
| 4-54 | Et | 2 | c-Pr | c-Bu |
| 4-55 | Et | 0 | CH$_2$c-Pr | c-Bu |
| 4-56 | Et | 1 | CH$_2$c-Pr | c-Bu |
| 4-57 | Et | 2 | CH$_2$c-Pr | c-Bu |
| 4-58 | Et | 0 | CH$_2$CH$_2$OMe | c-Bu |
| 4-59 | Et | 1 | CH$_2$CH$_2$OMe | c-Bu |
| 4-60 | Et | 2 | CH$_2$CH$_2$OMe | c-Bu |
| 4-61 | c-Pr | 0 | Me | c-Pr |
| 4-62 | c-Pr | 1 | Me | c-Pr |
| 4-63 | c-Pr | 2 | Me | c-Pr |
| 4-64 | c-Pr | 0 | Et | c-Pr |
| 4-65 | c-Pr | 1 | Et | c-Pr |
| 4-66 | c-Pr | 2 | Et | c-Pr |
| 4-67 | c-Pr | 0 | c-Pr | c-Pr |

TABLE 4-continued

Inventive compounds of the general formula (I) in which Q is Q2 and $R^x$ is a methyl group

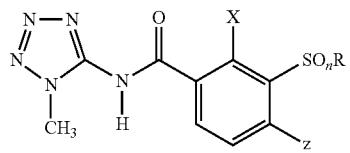

| No. | X | n | R | Z |
|---|---|---|---|---|
| 4-68 | c-Pr | 1 | c-Pr | c-Pr |
| 4-69 | c-Pr | 2 | c-Pr | c-Pr |
| 4-70 | c-Pr | 0 | CH$_2$c-Pr | c-Pr |
| 4-71 | c-Pr | 1 | CH$_2$c-Pr | c-Pr |
| 4-72 | c-Pr | 2 | CH$_2$c-Pr | c-Pr |
| 4-73 | c-Pr | 0 | CH$_2$CH$_2$OMe | c-Pr |
| 4-74 | c-Pr | 1 | CH$_2$CH$_2$OMe | c-Pr |
| 4-75 | c-Pr | 2 | CH$_2$CH$_2$OMe | c-Pr |
| 4-76 | c-Pr | 0 | Me | c-Bu |
| 4-77 | c-Pr | 1 | Me | c-Bu |
| 4-78 | c-Pr | 2 | Me | c-Bu |
| 4-79 | c-Pr | 0 | Et | c-Bu |
| 4-80 | c-Pr | 1 | Et | c-Bu |
| 4-81 | c-Pr | 2 | Et | c-Bu |
| 4-82 | c-Pr | 0 | c-Pr | c-Bu |
| 4-83 | c-Pr | 1 | c-Pr | c-Bu |
| 4-84 | c-Pr | 2 | c-Pr | c-Bu |
| 4-85 | c-Pr | 0 | CH$_2$c-Pr | c-Bu |
| 4-86 | c-Pr | 1 | CH$_2$c-Pr | c-Bu |
| 4-87 | c-Pr | 2 | CH$_2$c-Pr | c-Bu |
| 4-88 | c-Pr | 0 | CH$_2$CH$_2$OMe | c-Bu |
| 4-89 | c-Pr | 1 | CH$_2$CH$_2$OMe | c-Bu |
| 4-90 | c-Pr | 2 | CH$_2$CH$_2$OMe | c-Bu |

TABLE 5

Inventive compounds of the general formula (I) in which Q is Q3 and $R^y$ is a methyl group

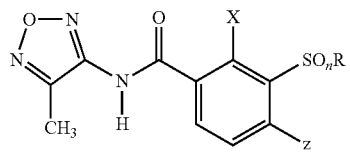

| No. | X | n | R | Z |
|---|---|---|---|---|
| 5-1 | Me | 0 | Me | c-Pr |
| 5-2 | Me | 1 | Me | c-Pr |
| 5-3 | Me | 2 | Me | c-Pr |
| 5-4 | Me | 0 | Et | c-Pr |
| 5-5 | Me | 1 | Et | c-Pr |
| 5-6 | Me | 2 | Et | c-Pr |
| 5-7 | Me | 0 | c-Pr | c-Pr |
| 5-8 | Me | 1 | c-Pr | c-Pr |
| 5-9 | Me | 2 | c-Pr | c-Pr |
| 5-10 | Me | 0 | CH$_2$c-Pr | c-Pr |
| 5-11 | Me | 1 | CH$_2$c-Pr | c-Pr |
| 5-12 | Me | 2 | CH$_2$c-Pr | c-Pr |
| 5-13 | Me | 0 | CH$_2$CH$_2$OMe | c-Pr |
| 5-14 | Me | 1 | CH$_2$CH$_2$OMe | c-Pr |
| 5-15 | Me | 2 | CH$_2$CH$_2$OMe | c-Pr |
| 5-16 | Me | 0 | Me | c-Bu |
| 5-17 | Me | 1 | Me | c-Bu |
| 5-18 | Me | 2 | Me | c-Bu |
| 5-19 | Me | 0 | Et | c-Bu |
| 5-20 | Me | 1 | Et | c-Bu |
| 5-21 | Me | 2 | Et | c-Bu |
| 5-22 | Me | 0 | c-Pr | c-Bu |
| 5-23 | Me | 1 | c-Pr | c-Bu |
| 5-24 | Me | 2 | c-Pr | c-Bu |
| 5-25 | Me | 0 | CH$_2$c-Pr | c-Bu |
| 5-26 | Me | 1 | CH$_2$c-Pr | c-Bu |

TABLE 5-continued

Inventive compounds of the general formula (I) in which Q is Q3 and $R^y$ is a methyl group

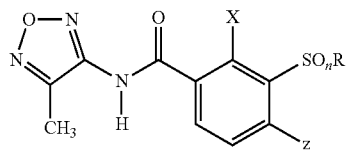

| No. | X | n | R | Z |
|---|---|---|---|---|
| 5-27 | Me | 2 | CH$_2$c-Pr | c-Bu |
| 5-28 | Me | 0 | CH$_2$CH$_2$OMe | c-Bu |
| 5-29 | Me | 1 | CH$_2$CH$_2$OMe | c-Bu |
| 5-30 | Me | 2 | CH$_2$CH$_2$OMe | c-Bu |
| 5-31 | Et | 0 | Me | c-Pr |
| 5-32 | Et | 1 | Me | c-Pr |
| 5-33 | Et | 2 | Me | c-Pr |
| 5-34 | Et | 0 | Et | c-Pr |
| 5-35 | Et | 1 | Et | c-Pr |
| 5-36 | Et | 2 | Et | c-Pr |
| 5-37 | Et | 0 | c-Pr | c-Pr |
| 5-38 | Et | 1 | c-Pr | c-Pr |
| 5-39 | Et | 2 | c-Pr | c-Pr |
| 5-40 | Et | 0 | CH$_2$c-Pr | c-Pr |
| 5-41 | Et | 1 | CH$_2$c-Pr | c-Pr |
| 5-42 | Et | 2 | CH$_2$c-Pr | c-Pr |
| 5-43 | Et | 0 | CH$_2$CH$_2$OMe | c-Pr |
| 5-44 | Et | 1 | CH$_2$CH$_2$OMe | c-Pr |
| 5-45 | Et | 2 | CH$_2$CH$_2$OMe | c-Pr |
| 5-46 | Et | 0 | Me | c-Bu |
| 5-47 | Et | 1 | Me | c-Bu |
| 5-48 | Et | 2 | Me | c-Bu |
| 5-49 | Et | 0 | Et | c-Bu |
| 5-50 | Et | 1 | Et | c-Bu |
| 5-51 | Et | 2 | Et | c-Bu |
| 5-52 | Et | 0 | c-Pr | c-Bu |
| 5-53 | Et | 1 | c-Pr | c-Bu |
| 5-54 | Et | 2 | c-Pr | c-Bu |
| 5-55 | Et | 0 | CH$_2$c-Pr | c-Bu |
| 5-56 | Et | 1 | CH$_2$c-Pr | c-Bu |
| 5-57 | Et | 2 | CH$_2$c-Pr | c-Bu |
| 5-58 | Et | 0 | CH$_2$CH$_2$OMe | c-Bu |
| 5-59 | Et | 1 | CH$_2$CH$_2$OMe | c-Bu |
| 5-60 | Et | 2 | CH$_2$CH$_2$OMe | c-Bu |
| 5-61 | c-Pr | 0 | Me | c-Pr |
| 5-62 | c-Pr | 1 | Me | c-Pr |
| 5-63 | c-Pr | 2 | Me | c-Pr |
| 5-64 | c-Pr | 0 | Et | c-Pr |
| 5-65 | c-Pr | 1 | Et | c-Pr |
| 5-66 | c-Pr | 2 | Et | c-Pr |
| 5-67 | c-Pr | 0 | c-Pr | c-Pr |
| 5-68 | c-Pr | 1 | c-Pr | c-Pr |
| 5-69 | c-Pr | 2 | c-Pr | c-Pr |
| 5-70 | c-Pr | 0 | CH$_2$c-Pr | c-Pr |
| 5-71 | c-Pr | 1 | CH$_2$c-Pr | c-Pr |
| 5-72 | c-Pr | 2 | CH$_2$c-Pr | c-Pr |
| 5-73 | c-Pr | 0 | CH$_2$CH$_2$OMe | c-Pr |
| 5-74 | c-Pr | 1 | CH$_2$CH$_2$OMe | c-Pr |
| 5-75 | c-Pr | 2 | CH$_2$CH$_2$OMe | c-Pr |
| 5-76 | c-Pr | 0 | Me | c-Bu |
| 5-77 | c-Pr | 1 | Me | c-Bu |
| 5-78 | c-Pr | 2 | Me | c-Bu |
| 5-79 | c-Pr | 0 | Et | c-Bu |
| 5-80 | c-Pr | 1 | Et | c-Bu |
| 5-81 | c-Pr | 2 | Et | c-Bu |
| 5-82 | c-Pr | 0 | c-Pr | c-Bu |
| 5-83 | c-Pr | 1 | c-Pr | c-Bu |
| 5-84 | c-Pr | 2 | c-Pr | c-Bu |
| 5-85 | c-Pr | 0 | CH$_2$c-Pr | c-Bu |
| 5-86 | c-Pr | 1 | CH$_2$c-Pr | c-Bu |
| 5-87 | c-Pr | 2 | CH$_2$c-Pr | c-Bu |
| 5-88 | c-Pr | 0 | CH$_2$CH$_2$OMe | c-Bu |
| 5-89 | c-Pr | 1 | CH$_2$CH$_2$OMe | c-Bu |
| 5-90 | c-Pr | 2 | CH$_2$CH$_2$OMe | c-Bu |

TABLE 6

Inventive compounds of the general formula (I) in which Q is Q3 and $R^y$ is a chlorine atom

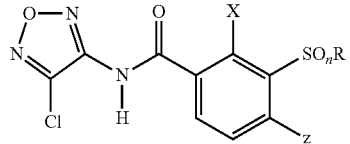

| No. | X | n | R | Z |
|---|---|---|---|---|
| 6-1 | Me | 0 | Me | c-Pr |
| 6-2 | Me | 1 | Me | c-Pr |
| 6-3 | Me | 2 | Me | c-Pr |
| 6-4 | Me | 0 | Et | c-Pr |
| 6-5 | Me | 1 | Et | c-Pr |
| 6-6 | Me | 2 | Et | c-Pr |
| 6-7 | Me | 0 | c-Pr | c-Pr |
| 6-8 | Me | 1 | c-Pr | c-Pr |
| 6-9 | Me | 2 | c-Pr | c-Pr |
| 6-10 | Me | 0 | $CH_2$c-Pr | c-Pr |
| 6-11 | Me | 1 | $CH_2$c-Pr | c-Pr |
| 6-12 | Me | 2 | $CH_2$c-Pr | c-Pr |
| 6-13 | Me | 0 | $CH_2CH_2OMe$ | c-Pr |
| 6-14 | Me | 1 | $CH_2CH_2OMe$ | c-Pr |
| 6-15 | Me | 2 | $CH_2CH_2OMe$ | c-Pr |
| 6-16 | Me | 0 | Me | c-Bu |
| 6-17 | Me | 1 | Me | c-Bu |
| 6-18 | Me | 2 | Me | c-Bu |
| 6-19 | Me | 0 | Et | c-Bu |
| 6-20 | Me | 1 | Et | c-Bu |
| 6-21 | Me | 2 | Et | c-Bu |
| 6-22 | Me | 0 | c-Pr | c-Bu |
| 6-23 | Me | 1 | c-Pr | c-Bu |
| 6-24 | Me | 2 | c-Pr | c-Bu |
| 6-25 | Me | 0 | $CH_2$c-Pr | c-Bu |
| 6-26 | Me | 1 | $CH_2$c-Pr | c-Bu |
| 6-27 | Me | 2 | $CH_2$c-Pr | c-Bu |
| 6-28 | Me | 0 | $CH_2CH_2OMe$ | c-Bu |
| 6-29 | Me | 1 | $CH_2CH_2OMe$ | c-Bu |
| 6-30 | Me | 2 | $CH_2CH_2OMe$ | c-Bu |
| 6-31 | Et | 0 | Me | c-Pr |
| 6-32 | Et | 1 | Me | c-Pr |
| 6-33 | Et | 2 | Me | c-Pr |
| 6-34 | Et | 0 | Et | c-Pr |
| 6-35 | Et | 1 | Et | c-Pr |
| 6-36 | Et | 2 | Et | c-Pr |
| 6-37 | Et | 0 | c-Pr | c-Pr |
| 6-38 | Et | 1 | c-Pr | c-Pr |
| 6-39 | Et | 2 | c-Pr | c-Pr |
| 6-40 | Et | 0 | $CH_2$c-Pr | c-Pr |
| 6-41 | Et | 1 | $CH_2$c-Pr | c-Pr |
| 6-42 | Et | 2 | $CH_2$c-Pr | c-Pr |
| 6-43 | Et | 0 | $CH_2CH_2OMe$ | c-Pr |
| 6-44 | Et | 1 | $CH_2CH_2OMe$ | c-Pr |
| 6-45 | Et | 2 | $CH_2CH_2OMe$ | c-Pr |
| 6-46 | Et | 0 | Me | c-Bu |
| 6-47 | Et | 1 | Me | c-Bu |
| 6-48 | Et | 2 | Me | c-Bu |
| 6-49 | Et | 0 | Et | c-Bu |
| 6-50 | Et | 1 | Et | c-Bu |
| 6-51 | Et | 2 | Et | c-Bu |
| 6-52 | Et | 0 | c-Pr | c-Bu |
| 6-53 | Et | 1 | c-Pr | c-Bu |
| 6-54 | Et | 2 | c-Pr | c-Bu |
| 6-55 | Et | 0 | $CH_2$c-Pr | c-Bu |
| 6-56 | Et | 1 | $CH_2$c-Pr | c-Bu |
| 6-57 | Et | 2 | $CH_2$c-Pr | c-Bu |
| 6-58 | Et | 0 | $CH_2CH_2OMe$ | c-Bu |
| 6-59 | Et | 1 | $CH_2CH_2OMe$ | c-Bu |
| 6-60 | Et | 2 | $CH_2CH_2OMe$ | c-Bu |
| 6-61 | c-Pr | 0 | Me | c-Pr |
| 6-62 | c-Pr | 1 | Me | c-Pr |
| 6-63 | c-Pr | 2 | Me | c-Pr |
| 6-64 | c-Pr | 0 | Et | c-Pr |
| 6-65 | c-Pr | 1 | Et | c-Pr |
| 6-66 | c-Pr | 2 | Et | c-Pr |
| 6-67 | c-Pr | 0 | c-Pr | c-Pr |

TABLE 6-continued

Inventive compounds of the general formula (I) in which Q is Q3 and $R^y$ is a chlorine atom

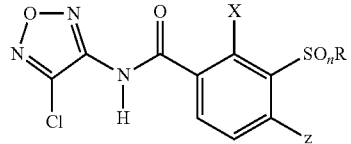

| No. | X | n | R | Z |
|---|---|---|---|---|
| 6-68 | c-Pr | 1 | c-Pr | c-Pr |
| 6-69 | c-Pr | 2 | c-Pr | c-Pr |
| 6-70 | c-Pr | 0 | $CH_2$c-Pr | c-Pr |
| 6-71 | c-Pr | 1 | $CH_2$c-Pr | c-Pr |
| 6-72 | c-Pr | 2 | $CH_2$c-Pr | c-Pr |
| 6-73 | c-Pr | 0 | $CH_2CH_2OMe$ | c-Pr |
| 6-74 | c-Pr | 1 | $CH_2CH_2OMe$ | c-Pr |
| 6-75 | c-Pr | 2 | $CH_2CH_2OMe$ | c-Pr |
| 6-76 | c-Pr | 0 | Me | c-Bu |
| 6-77 | c-Pr | 1 | Me | c-Bu |
| 6-78 | c-Pr | 2 | Me | c-Bu |
| 6-79 | c-Pr | 0 | Et | c-Bu |
| 6-80 | c-Pr | 1 | Et | c-Bu |
| 6-81 | c-Pr | 2 | Et | c-Bu |
| 6-82 | c-Pr | 0 | c-Pr | c-Bu |
| 6-83 | c-Pr | 1 | c-Pr | c-Bu |
| 6-84 | c-Pr | 2 | c-Pr | c-Bu |
| 6-85 | c-Pr | 0 | $CH_2$c-Pr | c-Bu |
| 6-86 | c-Pr | 1 | $CH_2$c-Pr | c-Bu |
| 6-87 | c-Pr | 2 | $CH_2$c-Pr | c-Bu |
| 6-88 | c-Pr | 0 | $CH_2CH_2OMe$ | c-Bu |
| 6-89 | c-Pr | 1 | $CH_2CH_2OMe$ | c-Bu |
| 6-90 | c-Pr | 2 | $CH_2CH_2OMe$ | c-Bu |

TABLE 7

Inventive compounds of the general formula (I) in which Q is Q4 and $R^z$ is a methyl group

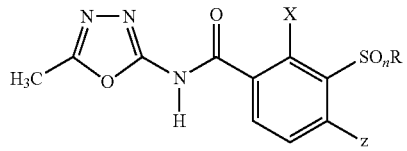

| No. | X | n | R | Z |
|---|---|---|---|---|
| 7-1 | Me | 0 | Me | c-Pr |
| 7-2 | Me | 1 | Me | c-Pr |
| 7-3 | Me | 2 | Me | c-Pr |
| 7-4 | Me | 0 | Et | c-Pr |
| 7-5 | Me | 1 | Et | c-Pr |
| 7-6 | Me | 2 | Et | c-Pr |
| 7-7 | Me | 0 | c-Pr | c-Pr |
| 7-8 | Me | 1 | c-Pr | c-Pr |
| 7-9 | Me | 2 | c-Pr | c-Pr |
| 7-10 | Me | 0 | $CH_2$c-Pr | c-Pr |
| 7-11 | Me | 1 | $CH_2$c-Pr | c-Pr |
| 7-12 | Me | 2 | $CH_2$c-Pr | c-Pr |
| 7-13 | Me | 0 | $CH_2CH_2OMe$ | c-Pr |
| 7-14 | Me | 1 | $CH_2CH_2OMe$ | c-Pr |
| 7-15 | Me | 2 | $CH_2CH_2OMe$ | c-Pr |
| 7-16 | Me | 0 | Me | c-Bu |
| 7-17 | Me | 1 | Me | c-Bu |
| 7-18 | Me | 2 | Me | c-Bu |
| 7-19 | Me | 0 | Et | c-Bu |
| 7-20 | Me | 1 | Et | c-Bu |
| 7-21 | Me | 2 | Et | c-Bu |
| 7-22 | Me | 0 | c-Pr | c-Bu |
| 7-23 | Me | 1 | c-Pr | c-Bu |
| 7-24 | Me | 2 | c-Pr | c-Bu |
| 7-25 | Me | 0 | $CH_2$c-Pr | c-Bu |
| 7-26 | Me | 1 | $CH_2$c-Pr | c-Bu |

TABLE 7-continued

Inventive compounds of the general formula (I) in which Q is Q4 and $R^z$ is a methyl group

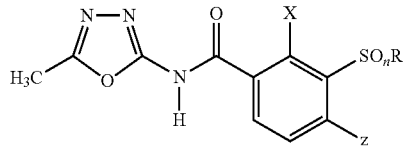

| No. | X | n | R | Z |
|---|---|---|---|---|
| 7-27 | Me | 2 | CH$_2$c-Pr | c-Bu |
| 7-28 | Me | 0 | CH$_2$CH$_2$OMe | c-Bu |
| 7-29 | Me | 1 | CH$_2$CH$_2$OMe | c-Bu |
| 7-30 | Me | 2 | CH$_2$CH$_2$OMe | c-Bu |
| 7-31 | Et | 0 | Me | c-Pr |
| 7-32 | Et | 1 | Me | c-Pr |
| 7-33 | Et | 2 | Me | c-Pr |
| 7-34 | Et | 0 | Et | c-Pr |
| 7-35 | Et | 1 | Et | c-Pr |
| 7-36 | Et | 2 | Et | c-Pr |
| 7-37 | Et | 0 | c-Pr | c-Pr |
| 7-38 | Et | 1 | c-Pr | c-Pr |
| 7-39 | Et | 2 | c-Pr | c-Pr |
| 7-40 | Et | 0 | CH$_2$c-Pr | c-Pr |
| 7-41 | Et | 1 | CH$_2$c-Pr | c-Pr |
| 7-42 | Et | 2 | CH$_2$c-Pr | c-Pr |
| 7-43 | Et | 0 | CH$_2$CH$_2$OMe | c-Pr |
| 7-44 | Et | 1 | CH$_2$CH$_2$OMe | c-Pr |
| 7-45 | Et | 2 | CH$_2$CH$_2$OMe | c-Pr |
| 7-46 | Et | 0 | Me | c-Bu |
| 7-47 | Et | 1 | Me | c-Bu |
| 7-48 | Et | 2 | Me | c-Bu |
| 7-49 | Et | 0 | Et | c-Bu |
| 7-50 | Et | 1 | Et | c-Bu |
| 7-51 | Et | 2 | Et | c-Bu |
| 7-52 | Et | 0 | c-Pr | c-Bu |
| 7-53 | Et | 1 | c-Pr | c-Bu |
| 7-54 | Et | 2 | c-Pr | c-Bu |
| 7-55 | Et | 0 | CH$_2$c-Pr | c-Bu |
| 7-56 | Et | 1 | CH$_2$c-Pr | c-Bu |
| 7-57 | Et | 2 | CH$_2$c-Pr | c-Bu |
| 7-58 | Et | 0 | CH$_2$CH$_2$OMe | c-Bu |
| 7-59 | Et | 1 | CH$_2$CH$_2$OMe | c-Bu |
| 7-60 | Et | 2 | CH$_2$CH$_2$OMe | c-Bu |
| 7-61 | c-Pr | 0 | Me | c-Pr |
| 7-62 | c-Pr | 1 | Me | c-Pr |
| 7-63 | c-Pr | 2 | Me | c-Pr |
| 7-64 | c-Pr | 0 | Et | c-Pr |
| 7-65 | c-Pr | 1 | Et | c-Pr |
| 7-66 | c-Pr | 2 | Et | c-Pr |
| 7-67 | c-Pr | 0 | c-Pr | c-Pr |
| 7-68 | c-Pr | 1 | c-Pr | c-Pr |
| 7-69 | c-Pr | 2 | c-Pr | c-Pr |
| 7-70 | c-Pr | 0 | CH$_2$c-Pr | c-Pr |
| 7-71 | c-Pr | 1 | CH$_2$c-Pr | c-Pr |
| 7-72 | c-Pr | 2 | CH$_2$c-Pr | c-Pr |
| 7-73 | c-Pr | 0 | CH$_2$CH$_2$OMe | c-Pr |
| 7-74 | c-Pr | 1 | CH$_2$CH$_2$OMe | c-Pr |
| 7-75 | c-Pr | 2 | CH$_2$CH$_2$OMe | c-Pr |
| 7-76 | c-Pr | 0 | Me | c-Bu |
| 7-77 | c-Pr | 1 | Me | c-Bu |
| 7-78 | c-Pr | 2 | Me | c-Bu |
| 7-79 | c-Pr | 0 | Et | c-Bu |
| 7-80 | c-Pr | 1 | Et | c-Bu |
| 7-81 | c-Pr | 2 | Et | c-Bu |
| 7-82 | c-Pr | 0 | c-Pr | c-Bu |
| 7-83 | c-Pr | 1 | c-Pr | c-Bu |
| 7-84 | c-Pr | 2 | c-Pr | c-Bu |
| 7-85 | c-Pr | 0 | CH$_2$c-Pr | c-Bu |
| 7-86 | c-Pr | 1 | CH$_2$c-Pr | c-Bu |
| 7-87 | c-Pr | 2 | CH$_2$c-Pr | c-Bu |
| 7-88 | c-Pr | 0 | CH$_2$CH$_2$OMe | c-Bu |
| 7-89 | c-Pr | 1 | CH$_2$CH$_2$OMe | c-Bu |
| 7-90 | c-Pr | 2 | CH$_2$CH$_2$OMe | c-Bu |

TABLE 8

Inventive compounds of the general formula (I) in the form of the sodium salts, in which Q is Q1 and $R^x$ is a methyl group

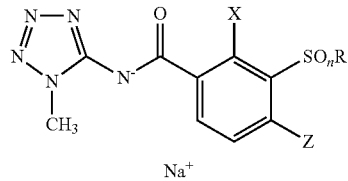

| No. | X | n | R | Z |
|---|---|---|---|---|
| 8-1 | Me | 0 | Me | c-Pr |
| 8-2 | Me | 1 | Me | c-Pr |
| 8-3 | Me | 2 | Me | c-Pr |
| 8-4 | Me | 0 | Et | c-Pr |
| 8-5 | Me | 1 | Et | c-Pr |
| 8-6 | Me | 2 | Et | c-Pr |
| 8-7 | Me | 0 | c-Pr | c-Pr |
| 8-8 | Me | 1 | c-Pr | c-Pr |
| 8-9 | Me | 2 | c-Pr | c-Pr |
| 8-10 | Me | 0 | CH$_2$c-Pr | c-Pr |
| 8-11 | Me | 1 | CH$_2$c-Pr | c-Pr |
| 8-12 | Me | 2 | CH$_2$c-Pr | c-Pr |
| 8-13 | Me | 0 | CH$_2$CH$_2$OMe | c-Pr |
| 8-14 | Me | 1 | CH$_2$CH$_2$OMe | c-Pr |
| 8-15 | Me | 2 | CH$_2$CH$_2$OMe | c-Pr |
| 8-16 | Me | 0 | Me | c-Bu |
| 8-17 | Me | 1 | Me | c-Bu |
| 8-18 | Me | 2 | Me | c-Bu |
| 8-19 | Me | 0 | Et | c-Bu |
| 8-20 | Me | 1 | Et | c-Bu |
| 8-21 | Me | 2 | Et | c-Bu |
| 8-22 | Me | 0 | c-Pr | c-Bu |
| 8-23 | Me | 1 | c-Pr | c-Bu |
| 8-24 | Me | 2 | c-Pr | c-Bu |
| 8-25 | Me | 0 | CH$_2$c-Pr | c-Bu |
| 8-26 | Me | 1 | CH$_2$c-Pr | c-Bu |
| 8-27 | Me | 2 | CH$_2$c-Pr | c-Bu |
| 8-28 | Me | 0 | CH$_2$CH$_2$OMe | c-Bu |
| 8-29 | Me | 1 | CH$_2$CH$_2$OMe | c-Bu |
| 8-30 | Me | 2 | CH$_2$CH$_2$OMe | c-Bu |
| 8-31 | Et | 0 | Me | c-Pr |
| 8-32 | Et | 1 | Me | c-Pr |
| 8-33 | Et | 2 | Me | c-Pr |
| 8-34 | Et | 0 | Et | c-Pr |
| 8-35 | Et | 1 | Et | c-Pr |
| 8-36 | Et | 2 | Et | c-Pr |
| 8-37 | Et | 0 | c-Pr | c-Pr |
| 8-38 | Et | 1 | c-Pr | c-Pr |
| 8-39 | Et | 2 | c-Pr | c-Pr |
| 8-40 | Et | 0 | CH$_2$c-Pr | c-Pr |
| 8-41 | Et | 1 | CH$_2$c-Pr | c-Pr |
| 8-42 | Et | 2 | CH$_2$c-Pr | c-Pr |
| 8-43 | Et | 0 | CH$_2$CH$_2$OMe | c-Pr |
| 8-44 | Et | 1 | CH$_2$CH$_2$OMe | c-Pr |
| 8-45 | Et | 2 | CH$_2$CH$_2$OMe | c-Pr |
| 8-46 | Et | 0 | Me | c-Bu |
| 8-47 | Et | 1 | Me | c-Bu |
| 8-48 | Et | 2 | Me | c-Bu |
| 8-49 | Et | 0 | Et | c-Bu |
| 8-50 | Et | 1 | Et | c-Bu |
| 8-51 | Et | 2 | Et | c-Bu |
| 8-52 | Et | 0 | c-Pr | c-Bu |
| 8-53 | Et | 1 | c-Pr | c-Bu |
| 8-54 | Et | 2 | c-Pr | c-Bu |
| 8-55 | Et | 0 | CH$_2$c-Pr | c-Bu |
| 8-56 | Et | 1 | CH$_2$c-Pr | c-Bu |
| 8-57 | Et | 2 | CH$_2$c-Pr | c-Bu |
| 8-58 | Et | 0 | CH$_2$CH$_2$OMe | c-Bu |
| 8-59 | Et | 1 | CH$_2$CH$_2$OMe | c-Bu |
| 8-60 | Et | 2 | CH$_2$CH$_2$OMe | c-Bu |
| 8-61 | c-Pr | 0 | Me | c-Pr |
| 8-62 | c-Pr | 1 | Me | c-Pr |
| 8-63 | c-Pr | 2 | Me | c-Pr |
| 8-64 | c-Pr | 0 | Et | c-Pr |
| 8-65 | c-Pr | 1 | Et | c-Pr |

TABLE 8-continued

Inventive compounds of the general formula (I) in the form of the sodium salts, in which Q is Q1 and R^x is a methyl group

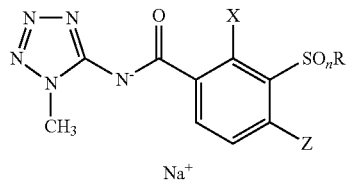

| No. | X | n | R | Z |
|---|---|---|---|---|
| 8-66 | c-Pr | 2 | Et | c-Pr |
| 8-67 | c-Pr | 0 | c-Pr | c-Pr |
| 8-68 | c-Pr | 1 | c-Pr | c-Pr |
| 8-69 | c-Pr | 2 | c-Pr | c-Pr |
| 8-70 | c-Pr | 0 | CH$_2$c-Pr | c-Pr |
| 8-71 | c-Pr | 1 | CH$_2$c-Pr | c-Pr |
| 8-72 | c-Pr | 2 | CH$_2$c-Pr | c-Pr |
| 8-73 | c-Pr | 0 | CH$_2$CH$_2$OMe | c-Pr |
| 8-74 | c-Pr | 1 | CH$_2$CH$_2$OMe | c-Pr |
| 8-75 | c-Pr | 2 | CH$_2$CH$_2$OMe | c-Pr |
| 8-76 | c-Pr | 0 | Me | c-Bu |
| 8-77 | c-Pr | 1 | Me | c-Bu |
| 8-78 | c-Pr | 2 | Me | c-Bu |
| 8-79 | c-Pr | 0 | Et | c-Bu |
| 8-80 | c-Pr | 1 | Et | c-Bu |
| 8-81 | c-Pr | 2 | Et | c-Bu |
| 8-82 | c-Pr | 0 | c-Pr | c-Bu |
| 8-83 | c-Pr | 1 | c-Pr | c-Bu |
| 8-84 | c-Pr | 2 | c-Pr | c-Bu |
| 8-85 | c-Pr | 0 | CH$_2$c-Pr | c-Bu |
| 8-86 | c-Pr | 1 | CH$_2$c-Pr | c-Bu |
| 8-87 | c-Pr | 2 | CH$_2$c-Pr | c-Bu |
| 8-88 | c-Pr | 0 | CH$_2$CH$_2$OMe | c-Bu |
| 8-89 | c-Pr | 1 | CH$_2$CH$_2$OMe | c-Bu |
| 8-90 | c-Pr | 2 | CH$_2$CH$_2$OMe | c-Bu |

TABLE 9

Inventive benzoic acids of the formula (II)

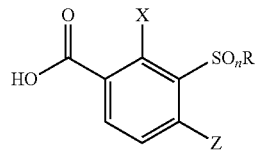

| No. | X | n | R | Z |
|---|---|---|---|---|
| 9-1 | Me | 0 | Me | c-Pr |
| 9-2 | Me | 1 | Me | c-Pr |
| 9-3 | Me | 2 | Me | c-Pr |
| 9-4 | Me | 0 | Et | c-Pr |
| 9-5 | Me | 1 | Et | c-Pr |
| 9-6 | Me | 2 | Et | c-Pr |
| 9-7 | Me | 0 | c-Pr | c-Pr |
| 9-8 | Me | 1 | c-Pr | c-Pr |
| 9-9 | Me | 2 | c-Pr | c-Pr |
| 9-10 | Me | 0 | CH$_2$c-Pr | c-Pr |
| 9-11 | Me | 1 | CH$_2$c-Pr | c-Pr |
| 9-12 | Me | 2 | CH$_2$c-Pr | c-Pr |
| 9-13 | Me | 0 | CH$_2$CH$_2$OMe | c-Pr |
| 9-14 | Me | 1 | CH$_2$CH$_2$OMe | c-Pr |
| 9-15 | Me | 2 | CH$_2$CH$_2$OMe | c-Pr |
| 9-16 | Me | 0 | Me | c-Bu |
| 9-17 | Me | 1 | Me | c-Bu |
| 9-18 | Me | 2 | Me | c-Bu |
| 9-19 | Me | 0 | Et | c-Bu |
| 9-20 | Me | 1 | Et | c-Bu |
| 9-21 | Me | 2 | Et | c-Bu |
| 9-22 | Me | 0 | c-Pr | c-Bu |
| 9-23 | Me | 1 | c-Pr | c-Bu |

TABLE 9-continued

Inventive benzoic acids of the formula (II)

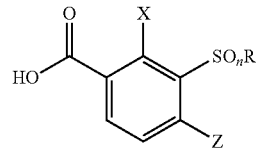

| No. | X | n | R | Z |
|---|---|---|---|---|
| 9-24 | Me | 2 | c-Pr | c-Bu |
| 9-25 | Me | 0 | CH$_2$c-Pr | c-Bu |
| 9-26 | Me | 1 | CH$_2$c-Pr | c-Bu |
| 9-27 | Me | 2 | CH$_2$c-Pr | c-Bu |
| 9-28 | Me | 0 | CH$_2$CH$_2$OMe | c-Bu |
| 9-29 | Me | 1 | CH$_2$CH$_2$OMe | c-Bu |
| 9-30 | Me | 2 | CH$_2$CH$_2$OMe | c-Bu |
| 9-31 | Et | 0 | Me | c-Pr |
| 9-32 | Et | 1 | Me | c-Pr |
| 9-33 | Et | 2 | Me | c-Pr |
| 9-34 | Et | 0 | Et | c-Pr |
| 9-35 | Et | 1 | Et | c-Pr |
| 9-36 | Et | 2 | Et | c-Pr |
| 9-37 | Et | 0 | c-Pr | c-Pr |
| 9-38 | Et | 1 | c-Pr | c-Pr |
| 9-39 | Et | 2 | c-Pr | c-Pr |
| 9-40 | Et | 0 | CH$_2$c-Pr | c-Pr |
| 9-41 | Et | 1 | CH$_2$c-Pr | c-Pr |
| 9-42 | Et | 2 | CH$_2$c-Pr | c-Pr |
| 9-43 | Et | 0 | CH$_2$CH$_2$OMe | c-Pr |
| 9-44 | Et | 1 | CH$_2$CH$_2$OMe | c-Pr |
| 9-45 | Et | 2 | CH$_2$CH$_2$OMe | c-Pr |
| 9-46 | Et | 0 | Me | c-Bu |
| 9-47 | Et | 1 | Me | c-Bu |
| 9-48 | Et | 2 | Me | c-Bu |
| 9-49 | Et | 0 | Et | c-Bu |
| 9-50 | Et | 1 | Et | c-Bu |
| 9-51 | Et | 2 | Et | c-Bu |
| 9-52 | Et | 0 | c-Pr | c-Bu |
| 9-53 | Et | 1 | c-Pr | c-Bu |
| 9-54 | Et | 2 | c-Pr | c-Bu |
| 9-55 | Et | 0 | CH$_2$c-Pr | c-Bu |
| 9-56 | Et | 1 | CH$_2$c-Pr | c-Bu |
| 9-57 | Et | 2 | CH$_2$c-Pr | c-Bu |
| 9-58 | Et | 0 | CH$_2$CH$_2$OMe | c-Bu |
| 9-59 | Et | 1 | CH$_2$CH$_2$OMe | c-Bu |
| 9-60 | Et | 2 | CH$_2$CH$_2$OMe | c-Bu |
| 9-61 | c-Pr | 0 | Me | c-Pr |
| 9-62 | c-Pr | 1 | Me | c-Pr |
| 9-63 | c-Pr | 2 | Me | c-Pr |
| 9-64 | c-Pr | 0 | Et | c-Pr |
| 9-65 | c-Pr | 1 | Et | c-Pr |
| 9-66 | c-Pr | 2 | Et | c-Pr |
| 9-67 | c-Pr | 0 | c-Pr | c-Pr |
| 9-68 | c-Pr | 1 | c-Pr | c-Pr |
| 9-69 | c-Pr | 2 | c-Pr | c-Pr |
| 9-70 | c-Pr | 0 | CH$_2$c-Pr | c-Pr |
| 9-71 | c-Pr | 1 | CH$_2$c-Pr | c-Pr |
| 9-72 | c-Pr | 2 | CH$_2$c-Pr | c-Pr |
| 9-73 | c-Pr | 0 | CH$_2$CH$_2$OMe | c-Pr |
| 9-74 | c-Pr | 1 | CH$_2$CH$_2$OMe | c-Pr |
| 9-75 | c-Pr | 2 | CH$_2$CH$_2$OMe | c-Pr |
| 9-76 | c-Pr | 0 | Me | c-Bu |
| 9-77 | c-Pr | 1 | Me | c-Bu |
| 9-78 | c-Pr | 2 | Me | c-Bu |
| 9-79 | c-Pr | 0 | Et | c-Bu |
| 9-80 | c-Pr | 1 | Et | c-Bu |
| 9-81 | c-Pr | 2 | Et | c-Bu |
| 9-82 | c-Pr | 0 | c-Pr | c-Bu |
| 9-83 | c-Pr | 1 | c-Pr | c-Bu |
| 9-84 | c-Pr | 2 | c-Pr | c-Bu |
| 9-85 | c-Pr | 0 | CH$_2$c-Pr | c-Bu |
| 9-86 | c-Pr | 1 | CH$_2$c-Pr | c-Bu |
| 9-87 | c-Pr | 2 | CH$_2$c-Pr | c-Bu |
| 9-88 | c-Pr | 0 | CH$_2$CH$_2$OMe | c-Bu |
| 9-89 | c-Pr | 1 | CH$_2$CH$_2$OMe | c-Bu |
| 9-90 | c-Pr | 2 | CH$_2$CH$_2$OMe | c-Bu |

TABLE 10

Inventive benzoyl chlorides of the formula (III)

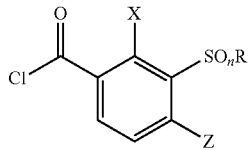

| No. | X | n | R | Z |
|---|---|---|---|---|
| 10-1 | Me | 0 | Me | c-Pr |
| 10-2 | Me | 2 | Me | c-Pr |
| 10-3 | Me | 0 | Et | c-Pr |
| 10-4 | Me | 2 | Et | c-Pr |
| 10-5 | Me | 0 | c-Pr | c-Pr |
| 10-6 | Me | 2 | c-Pr | c-Pr |
| 10-7 | Me | 0 | $CH_2$c-Pr | c-Pr |
| 10-8 | Me | 2 | $CH_2$c-Pr | c-Pr |
| 10-9 | Me | 0 | $CH_2CH_2OMe$ | c-Pr |
| 10-10 | Me | 2 | $CH_2CH_2OMe$ | c-Pr |
| 10-11 | Me | 0 | Me | c-Bu |
| 10-12 | Me | 2 | Me | c-Bu |
| 10-13 | Me | 0 | Et | c-Bu |
| 10-14 | Me | 2 | Et | c-Bu |
| 10-15 | Me | 0 | c-Pr | c-Bu |
| 10-16 | Me | 2 | c-Pr | c-Bu |
| 10-17 | Me | 0 | $CH_2$c-Pr | c-Bu |
| 10-18 | Me | 2 | $CH_2$c-Pr | c-Bu |
| 10-19 | Me | 0 | $CH_2CH_2OMe$ | c-Bu |
| 10-20 | Me | 2 | $CH_2CH_2OMe$ | c-Bu |
| 10-21 | Et | 0 | Me | c-Pr |
| 10-22 | Et | 2 | Me | c-Pr |
| 10-23 | Et | 0 | Et | c-Pr |
| 10-24 | Et | 2 | Et | c-Pr |
| 10-25 | Et | 0 | c-Pr | c-Pr |
| 10-26 | Et | 2 | c-Pr | c-Pr |
| 10-27 | Et | 0 | $CH_2$c-Pr | c-Pr |
| 10-28 | Et | 2 | $CH_2$c-Pr | c-Pr |
| 10-29 | Et | 0 | $CH_2CH_2OMe$ | c-Pr |
| 10-30 | Et | 2 | $CH_2CH_2OMe$ | c-Pr |
| 10-31 | Et | 0 | Me | c-Bu |
| 10-32 | Et | 2 | Me | c-Bu |
| 10-33 | Et | 0 | Et | c-Bu |
| 10-34 | Et | 2 | Et | c-Bu |
| 10-35 | Et | 0 | c-Pr | c-Bu |
| 10-36 | Et | 2 | c-Pr | c-Bu |
| 10-37 | Et | 0 | $CH_2$c-Pr | c-Bu |
| 10-38 | Et | 2 | $CH_2$c-Pr | c-Bu |
| 10-39 | Et | 0 | $CH_2CH_2OMe$ | c-Bu |
| 10-40 | Et | 2 | $CH_2CH_2OMe$ | c-Bu |
| 10-41 | c-Pr | 0 | Me | c-Pr |
| 10-42 | c-Pr | 2 | Me | c-Pr |
| 10-43 | c-Pr | 0 | Et | c-Pr |
| 10-44 | c-Pr | 2 | Et | c-Pr |
| 10-45 | c-Pr | 0 | c-Pr | c-Pr |
| 10-46 | c-Pr | 2 | c-Pr | c-Pr |
| 10-47 | c-Pr | 0 | $CH_2$c-Pr | c-Pr |
| 10-48 | c-Pr | 2 | $CH_2$c-Pr | c-Pr |
| 10-49 | c-Pr | 0 | $CH_2CH_2OMe$ | c-Pr |
| 10-50 | c-Pr | 2 | $CH_2CH_2OMe$ | c-Pr |
| 10-51 | c-Pr | 0 | Me | c-Bu |
| 10-52 | c-Pr | 2 | Me | c-Bu |
| 10-53 | c-Pr | 0 | Et | c-Bu |
| 10-54 | c-Pr | 2 | Et | c-Bu |
| 10-55 | c-Pr | 0 | c-Pr | c-Bu |
| 10-56 | c-Pr | 2 | c-Pr | c-Bu |
| 10-57 | c-Pr | 0 | $CH_2$c-Pr | c-Bu |
| 10-58 | c-Pr | 2 | $CH_2$c-Pr | c-Bu |
| 10-59 | c-Pr | 0 | $CH_2CH_2OMe$ | c-Bu |
| 10-60 | c-Pr | 2 | $CH_2CH_2OMe$ | c-Bu |

NMR data for numerous inventive compounds of the formulae (I) and (II) cited in the tables above are disclosed below using the NMR peak list method. The $^1$H NMR data of selected examples are stated here in the form of $^1$H NMR peak lists. For each signal peak, first the δ value in ppm and then the signal intensity in round brackets are listed. The pairs of δ value-signal intensity numbers for different signal peaks are listed with separation from one another by semicolons. The peak list for one example therefore has the form of:

$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum. The lists of the $^1$H NMR peaks are similar to the conventional $^1$H-NMR printouts and thus usually contain all peaks listed in a conventional NMR interpretation. In addition, like conventional $^1$H NMR printouts, they may show solvent signals, signals of stereoisomers of the target compounds which likewise form part of the subject matter of the invention, and/or peaks of impurities.

When stating compound signals in the delta range of solvents and/or water, in our lists of 1H NMR peaks, the usual solvent peaks, for example peaks of DMSO in DMSO-$D_6$ and the peak of water are shown, which usually have on average a high intensity.

The peaks of stereoisomers of the compounds of the invention and/or peaks of impurities usually have a lower intensity on average than the peaks of the compounds of the invention (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the compounds of the invention, optionally using additional intensity filters. This isolation would be similar to the peak picking in question in conventional $^1$H NMR interpretation.

Compounds of the formula (I):

Example 1-1

$^1$H-NMR (400.0 MHz, CDCl$_3$): δ=7.556 (0.8); 7.535 (0.8); 7.519 (0.6); 7.2694 (0.6); 7.2685 (0.6); 7.268 (0.8); 7.267 (1.0); 7.266 (1.1); 7.260 (117.2); 6.996 (0.6); 6.809 (0.9); 6.789 (0.9); 4.101 (11.9); 2.840 (0.8); 2.789 (7.6); 2.307 (16.0); 2.267 (0.7); 1.547 (4.4); 1.143 (1.2); 1.139 (1.1); 1.134 (0.6); 1.127 (0.7); 1.122 (1.1); 1.117 (1.2); 1.106 (0.6); 0.786 (0.5); 0.775 (1.2); 0.770 (1.2); 0.762 (1.1); 0.757 (1.3); 0.008 (1.5); 0.000 (54.5); −0.009 (1.5)

Example 1-2

$^1$H-NMR (400.0 MHz, CDCl$_3$): δ=9.854 (0.6); 7.605 (1.3); 7.584 (1.3); 7.519 (1.8); 7.260 (323.9); 6.996 (1.7); 6.933 (1.5); 6.912 (1.4); 4.103 (0.6); 4.088 (14.6); 3.022 (16.0); 2.831 (0.7); 2.708 (8.1); 2.307 (0.6); 2.096 (3.3); 1.545 (16.5); 1.254 (0.5); 1.195 (0.6); 1.177 (1.1); 1.156 (1.2); 0.881 (0.6); 0.867 (0.6); 0.858 (0.6); 0.805 (0.7); 0.796 (0.6); 0.008 (4.6); 0.000 (137.8); −0.009 (3.9); −0.150 (0.5)

Example 1-3

$^1$H-NMR (400.0 MHz, CDCl$_3$): δ=7.704 (0.8); 7.683 (0.9); 7.262 (29.8); 7.093 (1.1); 7.073 (1.0); 4.115 (8.3);

3.264 (16.0); 3.034 (0.8); 3.028 (0.6); 2.823 (8.5); 1.285 (0.7); 1.256 (3.3); 1.215 (0.7); 1.203 (1.6); 1.199 (1.6); 1.194 (0.9); 1.187 (0.9); 1.182 (1.5); 1.178 (1.5); 1.166 (0.6); 0.880 (0.8); 0.874 (0.9); 0.862 (1.9); 0.859 (2.0); 0.849 (1.8); 0.845 (1.8); 0.833 (0.7); 0.000 (13.3)

Example 2-1

$^1$H-NMR (400.0 MHz, CDCl$_3$): δ=7.542 (0.6); 7.519 (1.3); 7.260 (142.8); 6.996 (0.8); 6.800 (0.8); 6.780 (0.8); 4.486 (1.0); 4.468 (3.1); 4.450 (3.1); 4.432 (1.0); 2.850 (0.5); 2.836 (1.1); 2.829 (0.9); 2.823 (0.7); 2.815 (0.6); 2.785 (9.1); 2.310 (1.3); 2.304 (16.0); 2.264 (1.6); 2.044 (0.7); 1.637 (3.3); 1.619 (6.9); 1.600 (3.4); 1.591 (0.6); 1.573 (1.4); 1.555 (2.1); 1.259 (0.6); 1.151 (0.6); 1.140 (1.6); 1.135 (1.7); 1.130 (0.9); 1.124 (0.9); 1.119 (1.7); 1.114 (1.8); 1.103 (0.7); 0.882 (0.6); 0.782 (0.7); 0.770 (1.8); 0.766 (1.9); 0.757 (1.8); 0.753 (2.1); 0.741 (0.7); 0.008 (1.6); 0.000 (50.7); −0.009 (1.5)

Example 2-2

$^1$H-NMR (400.0 MHz, CDCl$_3$): δ=7.605 (1.1); 7.585 (1.2); 7.519 (1.2); 7.374 (0.5); 7.260 (199.6); 7.248 (0.6); 6.996 (1.2); 6.921 (1.5); 6.900 (1.4); 4.454 (0.8); 4.437 (2.1); 4.435 (2.2); 4.419 (2.2); 4.417 (2.2); 4.401 (0.8); 3.014 (16.0); 2.782 (0.8); 2.690 (7.5); 2.306 (1.5); 2.090 (0.8); 1.637 (0.6); 1.631 (3.9); 1.618 (1.2); 1.612 (8.6); 1.594 (4.1); 1.551 (3.2); 1.177 (1.4); 1.171 (0.9); 1.161 (0.9); 1.156 (1.4); 1.140 (0.5); 0.878 (0.5); 0.864 (0.6); 0.855 (0.6); 0.794 (0.6); 0.786 (0.6); 0.771 (0.5); 0.008 (2.4); 0.000 (71.6); −0.009 (2.1)

Example 2-3

$^1$H-NMR (400.0 MHz, CDCl$_3$): δ=7.687 (1.0); 7.666 (1.0); 7.271 (0.6); 7.270 (0.7); 7.269 (0.8); 7.268 (0.9); 7.261 (83.2); 7.095 (1.2); 7.074 (1.1); 4.501 (0.9); 4.482 (2.8); 4.464 (2.8); 4.446 (0.9); 3.264 (16.0); 3.043 (0.7); 2.834 (9.0); 2.006 (1.2); 1.642 (3.4); 1.624 (7.6); 1.606 (3.5); 1.574 (1.0); 1.219 (0.5); 1.207 (1.3); 1.202 (1.3); 1.198 (0.7); 1.191 (0.7); 1.185 (1.2); 1.181 (1.3); 1.170 (0.6); 0.873 (0.6); 0.862 (1.3); 0.858 (1.4); 0.848 (1.3); 0.844 (1.4); 0.008 (0.9); 0.000 (27.8); −0.009 (0.8)

Example 3-1

$^1$H-NMR (400.0 MHz, CDCl$_3$): δ=7.519 (1.3); 7.495 (0.7); 7.2763 (0.5); 7.2755 (0.6); 7.275 (0.6); 7.273 (0.7); 7.2723 (0.8); 7.2715 (0.9); 7.271 (1.0); 7.270 (1.1); 7.2683 (1.5); 7.2675 (1.7); 7.267 (1.9); 7.260 (158.8); 6.996 (0.9); 6.800 (0.9); 6.780 (0.9); 5.300 (4.4); 4.412 (1.4); 4.394 (1.8); 4.375 (1.5); 2.837 (0.7); 2.781 (7.0); 2.314 (0.6); 2.305 (16.0); 2.049 (0.8); 2.031 (1.5); 2.012 (1.5); 1.994 (0.9); 1.551 (2.0); 1.153 (0.5); 1.142 (1.3); 1.137 (1.3); 1.132 (0.7); 1.126 (0.7); 1.121 (1.3); 1.116 (1.3); 1.105 (0.6); 1.003 (3.1); 0.984 (6.6); 0.966 (3.0); 0.780 (0.6); 0.769 (1.3); 0.764 (1.4); 0.755 (1.3); 0.751 (1.5); 0.739 (0.5); 0.008 (2.0); 0.006 (0.8); 0.000 (60.1); −0.006 (0.7); −0.007 (0.5); −0.009 (1.7)

Example 3-2

$^1$H-NMR (400.0 MHz, CDCl$_3$): δ=7.584 (1.0); 7.564 (1.0); 7.519 (2.2); 7.292 (0.6); 7.276 (1.4); 7.273 (2.0); 7.260 (387.6); 7.252 (1.5); 7.250 (0.9); 7.249 (0.9); 7.210 (0.7); 6.996 (2.2); 6.927 (1.5); 6.907 (1.4); 4.384 (1.1); 4.381 (1.2); 4.366 (2.0); 4.361 (1.9); 4.347 (1.2); 4.344 (1.2); 3.247 (1.2); 3.016 (16.0); 2.834 (0.7); 2.702 (7.1); 2.093 (0.9); 2.044 (1.1); 2.025 (2.1); 2.007 (2.1); 1.988 (1.2); 1.548 (17.9); 1.189 (0.5); 1.174 (1.4); 1.168 (0.9); 1.153 (1.3); 1.007 (4.1); 0.995 (0.9); 0.989 (8.7); 0.970 (3.8); 0.860 (0.6); 0.851 (0.6); 0.799 (0.7); 0.791 (0.6); 0.008 (4.3); 0.000 (134.5); −0.009 (3.9)

Example 3-3

$^1$H-NMR (400.0 MHz, CDCl$_3$): δ=7.664 (1.0); 7.644 (1.1); 7.519 (0.7); 7.311 (0.8); 7.273 (1.0); 7.272 (0.9); 7.261 (126.8); 7.237 (1.0); 7.211 (0.6); 7.183 (1.0); 7.176 (0.5); 7.167 (0.6); 7.165 (0.7); 7.163 (0.7); 7.162 (0.6); 7.092 (1.2); 7.071 (1.2); 6.997 (0.8); 4.427 (1.5); 4.409 (1.9); 4.391 (1.5); 3.356 (0.6); 3.270 (0.8); 3.261 (16.0); 3.235 (0.5); 3.043 (0.8); 2.836 (9.4); 2.356 (3.7); 2.088 (1.2); 2.050 (0.9); 2.032 (1.6); 2.013 (1.7); 1.995 (1.0); 1.567 (1.1); 1.219 (0.5); 1.207 (1.3); 1.203 (1.4); 1.198 (0.8); 1.191 (0.8); 1.186 (1.3); 1.182 (1.4); 1.170 (0.6); 1.010 (3.5); 0.991 (7.4); 0.973 (3.3); 0.869 (0.6); 0.857 (1.4); 0.854 (1.6); 0.844 (1.4); 0.840 (1.5); 0.828 (0.6); 0.008 (1.4); 0.000 (45.9); −0.009 (1.4)

Example 4-1

$^1$H-NMR (400.0 MHz, CDCl$_3$): δ=7.519 (1.2); 7.494 (1.8); 7.456 (0.9); 7.436 (0.9); 7.260 (214.1); 6.996 (1.1); 6.777 (1.0); 6.756 (1.0); 3.880 (10.0); 2.830 (0.7); 2.757 (8.3); 2.297 (16.0); 2.045 (0.6); 1.542 (13.1); 1.146 (0.5); 1.134 (1.2); 1.130 (1.2); 1.125 (0.6); 1.118 (0.7); 1.113 (1.2); 1.108 (1.1); 1.097 (0.5); 0.768 (0.5); 0.757 (1.2); 0.752 (1.2); 0.743 (1.1); 0.739 (1.3); 0.008 (2.8); 0.000 (95.1); −0.009 (2.6)

Example 4-2

$^1$H-NMR (400.0 MHz, d$_6$-DMSO): δ=10.987 (1.4); 7.877 (2.3); 7.562 (0.7); 7.543 (0.8); 7.048 (1.1); 7.028 (1.1); 3.743 (16.0); 3.420 (0.5); 3.390 (0.5); 3.359 (0.7); 3.354 (0.9); 3.350 (1.0); 3.320 (733.1); 3.297 (31.4); 3.270 (1.4); 3.174 (0.7); 3.161 (0.7); 3.018 (14.4); 2.863 (0.5); 2.844 (0.6); 2.675 (1.3); 2.670 (1.8); 2.665 (1.4); 2.661 (0.8); 2.646 (9.4); 2.540 (1.1); 2.523 (4.9); 2.519 (7.6); 2.510 (96.8); 2.506 (208.5); 2.501 (288.8); 2.496 (201.8); 2.492 (89.9); 2.474 (1.2); 2.469 (1.1); 2.460 (0.8); 2.456 (0.8); 2.451 (0.9); 2.447 (0.5); 2.337 (0.5); 2.332 (1.2); 2.328 (1.7); 2.323 (1.3); 2.299 (0.5); 1.094 (0.5); 1.085 (0.6); 0.999 (0.5); 0.926 (0.6); 0.913 (0.7); 0.735 (0.6); 0.720 (0.6); 0.000 (0.5)

Example 4-3

$^1$H-NMR (400.0 MHz, CDCl$_3$): δ=7.604 (0.8); 7.584 (0.9); 7.410 (1.1); 7.261 (52.3); 7.063 (1.1); 7.042 (1.1); 3.890 (9.3); 3.230 (16.0); 3.042 (0.7); 2.815 (9.1); 2.055 (0.9); 1.285 (0.6); 1.255 (1.8); 1.212 (0.6); 1.200 (1.4); 1.196 (1.4); 1.191 (0.8); 1.184 (0.8); 1.179 (1.4); 1.175 (1.4); 1.163 (0.7); 0.849 (0.7); 0.837 (1.5); 0.834 (1.6); 0.824 (1.4); 0.820 (1.5); 0.808 (0.5); 0.008 (0.7); 0.000 (23.5); −0.009 (0.7)

Example 7-1

$^1$H-NMR (400.0 MHz, CDCl$_3$): δ=7.261 (70.3); 6.751 (1.2); 6.731 (1.2); 5.300 (1.6); 2.821 (0.9); 2.762 (11.2);

2.543 (10.9); 2.296 (16.0); 2.007 (7.2); 1.561 (2.5); 1.133 (0.6); 1.121 (1.4); 1.117 (1.4); 1.112 (0.8); 1.105 (0.8); 1.100 (1.4); 1.095 (1.4); 1.084 (0.6); 0.759 (0.7); 0.748 (1.6); 0.744 (1.6); 0.735 (1.5); 0.731 (1.6); 0.719 (0.5); 0.008 (0.9); 0.000 (28.7); −0.009 (0.7)

Example 7-2

$^1$H-NMR (400.0 MHz, CDCl$_3$): δ=7.532 (0.7); 7.520 (0.7); 7.511 (0.8); 7.261 (98.5); 7.228 (0.7); 6.997 (0.5); 6.871 (1.5); 6.851 (1.4); 3.001 (16.0); 2.655 (7.4); 2.547 (15.5); 1.333 (0.7); 1.285 (1.0); 1.255 (0.7); 1.119 (0.6); 1.110 (0.7); 1.106 (0.6); 1.097 (0.8); 1.087 (0.5); 1.076 (0.5); 0.834 (0.6); 0.768 (0.5); 0.758 (0.6); 0.74458 (0.5); 0.008 (1.0); 0.000 (34.6); −0.009 (1.0)

Example 7-3

$^1$H-NMR (400.0 MHz, d$_6$-DMSO): δ=12.049 (4.0); 7.606 (13.5); 7.586 (15.1); 7.145 (13.9); 7.124 (12.9); 5.755 (10.3); 3.352 (147.7); 3.314 (712.8); 3.290 (37.0); 2.894 (7.6); 2.880 (4.2); 2.674 (6.3); 2.670 (9.0); 2.665 (6.6); 2.638 (96.5); 2.539 (10.8); 2.534 (12.5); 2.530 (10.5); 2.523 (23.2); 2.518 (34.1); 2.510 (496.8); 2.505 (1075.7); 2.501 (1494.7); 2.496 (1040.4); 2.491 (467.1); 2.475 (130.1); 2.332 (5.6); 2.328 (8.5); 2.323 (6.0); 2.073 (13.1); 1.335 (2.9); 1.298 (3.0); 1.259 (4.6); 1.250 (4.7); 1.235 (4.9); 1.118 (4.6); 1.107 (12.3); 1.102 (13.3); 1.091 (7.4); 1.086 (13.0); 1.081 (13.4); 1.070 (5.8); 0.864 (5.7); 0.848 (16.0); 0.835 (14.5); 0.824 (4.3); 0.034 (2.6); 0.008 (15.2); 0.000 (516.1); −0.009 (15.7)

Compounds of the Formula (II):

Example 9-1

$^1$H-NMR (400.0 MHz, de-DMSO):
δ=7.628 (1.5); 7.608 (1.6); 6.806 (1.3); 6.785 (1.2); 3.320 (3.2); 2.772 (0.6); 2.749 (9.5); 2.737 (0.9); 2.723 (0.5); 2.511 (4.4); 2.507 (9.5); 2.502 (13.3); 2.498 (9.6); 2.493 (4.7); 2.478 (0.6); 2.258 (16.0); 2.029 (0.7); 1.078 (1.2); 1.072 (1.3); 1.068 (0.7); 1.062 (0.7); 1.057 (1.3); 1.051 (1.3); 1.041 (0.6); 0.752 (0.5); 0.741 (1.3); 0.736 (1.4); 0.728 (1.3); 0.723 (1.4); 0.712 (0.5); 0.000 (5.4)

B. FORMULATION EXAMPLES a) A dusting product is obtained by mixing 10 parts by weight of a compound of the formula (I) and/or salts thereof and 90 parts by weight of talc as an inert substance and comminuting the mixture in a hammer mill.
b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.
c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277 C), and grinding the mixture in a friction ball mill to a fineness of below 5 microns.
d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.
e) Water-dispersible granules are obtained by mixing
 75 parts by weight of a compound of the formula (I) and/or salts thereof,
 10 parts by weight of calcium lignosulfonate,
 5 parts by weight of sodium lauryl sulfate,
 3 parts by weight of polyvinyl alcohol and
 7 parts by weight of kaolin,
 grinding the mixture in a pinned-disk mill, and granulating the powder in a
 fluidized bed by spray application of water as a granulating liquid.
f) Water-dispersible granules are also obtained by homogenizing and precomminuting, in a colloid mill,
 25 parts by weight of a compound of the formula (I) and/or salts thereof,
 5 parts by weight of sodium 2,2'-dinaphthylmethane-6,6'-disulfonate
 2 parts by weight of sodium oleoylmethyltaurate,
 1 part by weight of polyvinyl alcohol
 17 parts by weight of calcium carbonate and
 50 parts by weight of water,
 then grinding the mixture in a bead mill and atomizing and drying the resulting suspension in a spray tower by means of a one-phase nozzle.

C. BIOLOGICAL EXAMPLES

The abbreviations used here are:

| ABUTH | Abutilon theophrasti | ALOMY | Alopecurus myosuroides |
|---|---|---|---|
| AMARE | Amaranthus retroflexus | AVEFA | Avena fatua |
| CYPES | Cyperus serotinus | ECHCG | Echinochloa crus galli |
| LOLMU | Lolium multiflorum | MATIN | Matricaria inodora |
| PHBPU | Pharbitis purpureum | PHBPU | Pharbitis purpureum |
| POLCO | Polygonum convolvulus | STEME | Stellaria media |
| VERPE | Veronica persica | | |

1. Pre-Emergence Herbicidal Action Against Harmful Plants

Seeds of monocotyledonous and dicotyledonous weed plants and crop plants are laid out in wood-fiber pots in sandy loam and covered with soil. The compounds of the invention and, for comparative purposes, the compounds known from the prior art, formulated in the form of wettable powders (WP) or as emulsion concentrates (EC), are then applied to the surface of the covering soil as aqueous suspension or emulsion at a water application rate equating to 600 to 800 I/ha with addition of 0.2% of wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants).

The experiments show that the compounds of the invention tested have higher herbicidal action against numerous harmful plants and have lower damage in crop plants than the structurally closest compounds known from the prior art. The data from these experiments are listed in the following tables:

TABLE A

| Compound | Dosage [g/ha] | Activity against CYPES | Activity against POLCO |
|---|---|---|---|
| Inventive compound no. 1-1 | 320 | 90% | 90% |
| Compound no. 4-78 known from WO 2012/028579 A1 | 320 | 30% | 0% |
| Compound no. 4-122 known from WO 2012/028579 A1 | 320 | 0% | 70% |

TABLE B

| Compound | Dosage [g/ha] | Activity against CYPES | Activity against POLCO |
|---|---|---|---|
| Inventive compound no. 1-1 | 320 | 90% | 90% |
| Compound no. 4-128 known from WO 2012/028579 A1 | 320 | 0% | 20% |
| Compound no. 4-429 known from WO 2012/028579 A1 | 320 | 30% | 0% |

TABLE B-continued

| Compound | Dosage [g/ha] | Activity against CYPES | POLCO |
|---|---|---|---|
| *[Structure: N-(1-methyl-1H-tetrazol-5-yl)-2-methyl-3-(methylthio)-4-(1,3-dioxolan-2-yl)benzamide]*<br>Compound known from WO 2012/028579 A1 | 320 | 0% | 30% |
| *[Structure: N-(1-methyl-1H-tetrazol-5-yl)-2-methyl-3-(methylthio)-4-formylbenzamide]*<br>Compound known from WO 2012/028579 A1 | 320 | 0% | 0% |

TABLE C

| Compound | Dosage [g/ha] | Activity against ALOMY | AMARE |
|---|---|---|---|
| *[Structure: N-(1-methyl-1H-tetrazol-5-yl)-2-methyl-3-(methylsulfinyl)-4-cyclopropylbenzamide]*<br>Inventive compound no. 1-2 | 320 | 90% | 100% |
| *[Structure: N-(1-methyl-1H-tetrazol-5-yl)-2-methyl-3-(methylthio)benzamide]*<br>Compound no. 4-79 known from WO 2012/028579 A1 | 320 | 20% | 20% |
| *[Structure: N-(1-methyl-1H-tetrazol-5-yl)-2-methyl-3-(methylthio)-4-(1,3-dioxolan-2-yl)benzamide]*<br>Compound known from WO 2012/028579 A1 | 320 | 0% | 0% |
| *[Structure: N-(1-methyl-1H-tetrazol-5-yl)-2-methyl-3-(methylthio)-4-formylbenzamide]*<br>Compound known from WO 2012/028579 A1 | 320 | 0% | 0% |

TABLE D
| Compound | Dosage [g/ha] | Activity against ALOMY | POLCO |
|---|---|---|---|
| 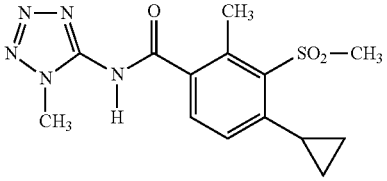 Inventive compound no. 1-3 | 320 | 100% | 90% |
| 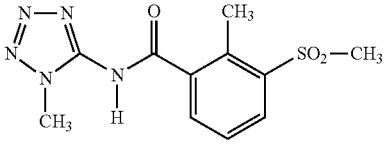 Compound no. 4-79 known from WO 2012/028579 A1 | 320 | 70% | 40% |
| 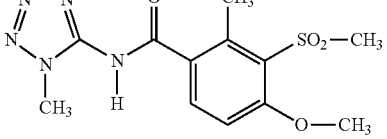 Compound no. 4-439 known from WO 2012/028579 A1 | 320 | 20% | 60% |
| 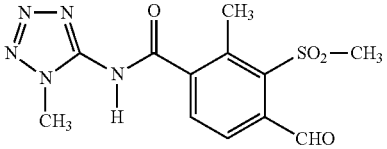 Compound known from WO 2012/028579 A1 | 320 | 0% | 60% |
TABLE E
| Compound | Dosage [g/ha] | Activity against AMARE | VERPE |
|---|---|---|---|
| 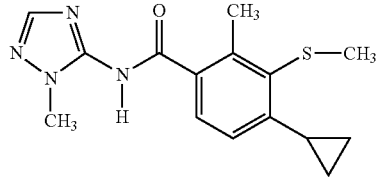 Inventive compound no. 4-1 | 320 | 100% | 90% |
| 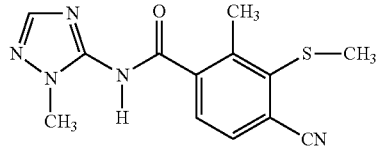 Compound no. 1-387 known from WO 2012/028579 A1 | 320 | 80% | 70% |

TABLE E-continued

| Compound | Dosage [g/ha] | Activity against AMARE | VERPE |
|---|---|---|---|
| Compound no. 1-139 known from WO 2012/028579 A1 (triazole-NHC(O)-benzamide with 2-CH₃, 3-SCH₃, 4-I) | 320 | 60% | 0% |
| Compound known from WO 2012/028579 A1 (triazole-NHC(O)-benzamide with 2-CH₃, 3-SCH₃, 4-CHO) | 320 | 30% | 0% |
| Compound known from WO 2012/028579 A1 (triazole-NHC(O)-benzamide with 2-CH₃, 3-SCH₃, 4-(1,3-dioxolan-2-yl)) | 320 | 0% | 0% |

TABLE F

| Compound | Dosage [g/ha] | Activity against AMARE | MATIN |
|---|---|---|---|
| Inventive compound no. 4-2 (triazole-NHC(O)-benzamide with 2-CH₃, 3-SOCH₃, 4-cyclopropyl) | 320 | 90% | 80% |
| Compound no. 1-120 known from WO 2012/028579 A1 (triazole-NHC(O)-benzamide with 2-CH₃, 3-SOCH₃, 4-Cl) | 320 | 70% | 30% |
| Compound no. 1-388 known from WO 2012/028579 A1 (triazole-NHC(O)-benzamide with 2-CH₃, 3-SOCH₃, 4-CN) | 320 | 60% | 0% |

TABLE F-continued

| Compound | Dosage [g/ha] | Activity against AMARE | Activity against MATIN |
|---|---|---|---|
| *N-(1-methyl-1H-1,2,4-triazol-3-yl)-2-methyl-3-(methylsulfinyl)-4-formylbenzamide*<br>Compound known from WO 2012/028579 A1 | 320 | 40% | 0% |
| *N-(1-methyl-1H-1,2,4-triazol-3-yl)-2-methyl-3-(methylsulfinyl)-4-(1,3-dioxolan-2-yl)benzamide*<br>Compound known from WO 2012/028579 A1 | 320 | 20% | 0% |

TABLE G

| Compound | Dosage [g/ha] | Activity against ECHCG | Activity against AMARE |
|---|---|---|---|
| *N-(1-methyl-1H-1,2,4-triazol-3-yl)-2-methyl-3-(methylsulfonyl)-4-cyclopropylbenzamide*<br>Inventive compound no. 4-3 | 320 | 90% | 100% |
| *N-(1-methyl-1H-1,2,4-triazol-3-yl)-2-methyl-3-(methylsulfonyl)benzamide*<br>Compound no. 1-90 known from WO 2012/028579 A1 | 320 | 30% | 10% |
| *N-(1-methyl-1H-1,2,4-triazol-3-yl)-2-methyl-3,4-bis(methylsulfonyl)benzamide*<br>Compound no. 1-88 known from WO 2012/028579 A1 | 320 | 0% | 40% |
| *N-(1-methyl-1H-1,2,4-triazol-3-yl)-2-methyl-3-(methylsulfonyl)-4-formylbenzamide*<br>Compound known from WO 2012/028579 A1 | 320 | 20% | 0% |

TABLE G-continued

| Compound | Dosage [g/ha] | Activity against | |
|---|---|---|---|
| | | ECHCG | AMARE |
| [structure] Compound known from WO 2012/028579 A1 | 320 | 40% | 60% |

TABLE H

| Compound | Dosage [g/ha] | Activity against | |
|---|---|---|---|
| | | AVEFA | LOLMU |
| [structure] Inventive compound no. 2-1 | 320 | 100% | 90% |
| [structure] Compound known from WO 2012/028579 A1 | 320 | 60% | 30% |

TABLE I

| Compound | Dosage [g/ha] | Activity against | |
|---|---|---|---|
| | | LOLMU | PHBPU |
| [structure] Inventive compound no. 2-2 | 320 | 100% | 100% |
| [structure] Compound no. 5-391 known from WO 2012/028579 A1 | 320 | 30% | 60% |

TABLE J

| Compound | Dosage [g/ha] | Activity against CYPES | ABUTH |
|---|---|---|---|
| Inventive compound no. 2-3 | 80 | 80% | 100% |
| Compound known from WO 2012/028579 A1 | 80 | 40% | 80% |

2. Post-Emergence Herbicidal Action Against Harmful Plants

Seeds of monocotyledonous and dicotyledonous weed and crop plants are laid out in sandy loam in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants in the form of an aqueous suspension or emulsion at a water application rate equating to 600 to 800 l/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). The experiments show that the compounds of the invention tested have higher herbicidal action against numerous harmful plants and have lower damage in crop plants than the structurally closest compounds known from the prior art. The data from these experiments are listed in the following tables:

TABLE K

| Compound | Dosage [g/ha] | Activity against MATIN | STEME |
|---|---|---|---|
| Inventive compound no. 7-1 | 80 | 80% | 90% |
| Compound no. 2-116 known from WO 2012/126932 A1 | 80 | 60% | 70% |

TABLE K-continued

| | Dosage | Activity against | |
|---|---|---|---|
| Compound | [g/ha] | MATIN | STEME |
| Compound no. 2-130 known from WO 2012/126932 A1 (5-methyl-1,3,4-oxadiazol-2-yl amide of 4-bromo-2-methyl-3-methylthiobenzamide) | 80 | 40% | 60% |

TABLE L

| | Dosage | Activity against | |
|---|---|---|---|
| Compound | [g/ha] | MATIN | POLCO |
| Inventive compound no. 7-1 (5-methyl-1,3,4-oxadiazol-2-yl amide of 4-cyclopropyl-2-methyl-3-methylthiobenzamide) | 80 | 80% | 60% |
| Compound no. 2-136 known from WO 2012/126932 A1 (5-methyl-1,3,4-oxadiazol-2-yl amide of 4-iodo-2-methyl-3-methylthiobenzamide) | 80 | 60% | 20% |
| Compound no. 2-143 known from WO 2012/126932 A1 (5-methyl-1,3,4-oxadiazol-2-yl amide of 2-methyl-3-methylthio-4-trifluoromethylbenzamide) | 80 | 60% | 0% |

The invention claimed is:

1. A benzamide of formula (I) or salt thereof

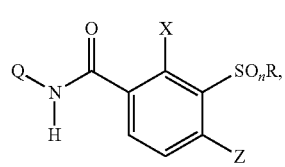

where the symbols and indices are each defined as follows:

Q is a Q1, Q2, Q3 or Q4 radical,

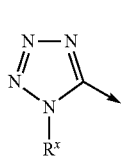

-continued

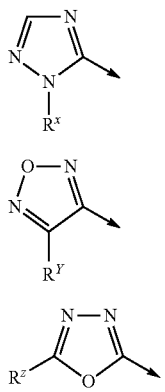

(Q2)

(Q3)

(Q4)

X is (C$_1$-C$_6$)-alkyl or (C$_3$-C$_6$)-cycloalkyl,
Z is (C$_3$-C$_6$)-cycloalkyl,
R is (C$_1$-C$_6$)-alkyl, (C$_3$-C$_6$)-cycloalkyl, (C$_3$-C$_6$)-cycloalkyl-(C$_1$-C$_6$)-alkyl, (C$_1$-C$_6$)-alkyl-O—(C$_1$-C$_6$)-alkyl,
R$^X$ is methyl, ethyl, n-propyl, prop-2-en-1-yl, methoxyethyl, ethoxyethyl or methoxyethoxyethyl,
R$^Y$ is methyl, ethyl, n-propyl, chlorine or amino,
R$^Z$ is methyl, ethyl, n-propyl or methoxymethyl,
n is 0, 1 or 2.

2. A benzamide or salt as claimed in claim 1, wherein Q is a Q1, Q2, Q3 or Q4 radical,

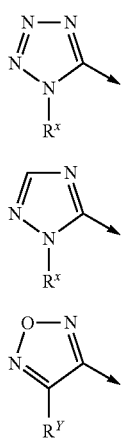

(Q1)

(Q2)

(Q3)

-continued (Q4)

X is methyl, ethyl or cyclopropyl,
Z is cyclopropyl or cyclobutyl,
R is methyl, ethyl, cyclopropyl, cyclopropylmethyl or methoxyethyl,
R$^X$ is methyl, ethyl, n-propyl, prop-2-en-1-yl, methoxyethyl, ethoxyethyl or methoxyethoxyethyl,
R$^Y$ is methyl, ethyl, n-propyl, chlorine or amino,
R$^Z$ is methyl, ethyl, n-propyl or methoxymethyl,
n is 0, 1 or 2.

3. The benzamide or salt according to claim 1, wherein Q is (Q1)

X is methyl,
Z is cyclopropyl,
R is methyl,
R$^X$ is methyl, and
n is 0.

4. A herbicidal composition comprising a herbicidally active content of at least one compound of the formula (I) or salt as claimed in claim 1.

5. The herbicidal composition as claimed in claim 4 in a mixture with one or more formulation auxiliaries.

6. A method of controlling unwanted plants, comprising applying an effective amount of at least one compound of formula (I) or salt as claimed in claim 1 or a herbicidal composition thereof to one or more plants or to a site of unwanted vegetation.

7. The method according to claim 6, wherein the one or more plants are useful plants.

8. The method as claimed in claim 7, wherein the useful plants are transgenic useful plants.

9. A product comprising a compound of formula (I) or salt as claimed in claim 1 or a herbicidal composition thereof for controlling one or more unwanted plants.

* * * * *